(12) United States Patent
Dobak, III et al.

(10) Patent No.: US 7,651,518 B2
(45) Date of Patent: Jan. 26, 2010

(54) INFLATABLE CATHETER FOR SELECTIVE ORGAN HEATING AND COOLING AND METHOD OF USING THE SAME

(75) Inventors: John D. Dobak, III, La Jolla, CA (US); Juan C. Lasheras, La Jolla, CA (US)

(73) Assignee: Innercool Therapies, Inc., San Diego, CA (US)

( * ) Notice: Subject to any disclaimer, the term of this patent is extended or adjusted under 35 U.S.C. 154(b) by 0 days.

(21) Appl. No.: 10/714,070

(22) Filed: Nov. 14, 2003

(65) Prior Publication Data

US 2004/0106969 A1 Jun. 3, 2004

Related U.S. Application Data

(60) Continuation of application No. 10/095,753, filed on Mar. 11, 2002, now Pat. No. 6,695,873, which is a division of application No. 09/757,124, filed on Jan. 8, 2001, now Pat. No. 6,540,771, which is a division of application No. 09/215,038, filed on Dec. 16, 1998, now Pat. No. 6,261,312, which is a continuation-in-part of application No. 09/103,342, filed on Jun. 23, 1998, now Pat. No. 6,096,068, which is a continuation-in-part of application No. 09/047,012, filed on Mar. 24, 1998, now Pat. No. 5,957,963, which is a continuation-in-part of application No. 09/012,287, filed on Jan. 23, 1998, now Pat. No. 6,051,019.

(51) Int. Cl.
*A61F 7/00* (2006.01)
(52) U.S. Cl. .................. 607/105; 607/106; 607/113
(58) Field of Classification Search ............ 606/20–26; 607/104–106; 604/7, 8
See application file for complete search history.

(56) References Cited

U.S. PATENT DOCUMENTS

| | | | |
|---|---|---|---|
| 2,308,484 A | 1/1943 | Auzin, et al. |
| 2,374,609 A | 4/1945 | McCollum |
| 2,615,686 A | 10/1952 | Davidson |
| 2,672,032 A | 3/1954 | Towse |

(Continued)

FOREIGN PATENT DOCUMENTS

AU 730835 B2 3/2001

(Continued)

OTHER PUBLICATIONS

Ambrus; *The Biphasic Nature and Temperature Dependence of the Activation of Human Plasminogen by Urokinase*; May 1979; pp. 339-347; Research Communications in Chemical Pathology and Pharmacology, vol. 24, No. 2.

(Continued)

*Primary Examiner*—Lee S Cohen

(57) ABSTRACT

A catheter system and method are provided which change the temperature of a fluid, such as blood, by heat transfer. Selective cooling or heating of an organ may be performed by changing the temperature of the blood feeding the organ. The catheter system includes an inlet lumen and an outlet lumen structured and arranged to carry a working fluid having a temperature different from the adjacent blood. The outlet lumen is configured to induce turbulence in the adjacent fluid passing adjacent the outlet lumen.

18 Claims, 6 Drawing Sheets

U.S. PATENT DOCUMENTS

| | | |
|---|---|---|
| 2,913,009 A | 11/1959 | Kuthe |
| 3,125,096 A | 3/1964 | Antiles et al. |
| 3,298,371 A | 1/1967 | Lee |
| 3,425,419 A | 2/1969 | Dato |
| 3,460,538 A | 8/1969 | Armstrong |
| 3,504,674 A | 4/1970 | Swenson, et al. |
| 3,604,419 A | 9/1971 | Diskin, et al. |
| 3,612,175 A | 10/1971 | Ford et al. |
| 3,865,116 A | 2/1975 | Brooks |
| 3,888,259 A | 6/1975 | Miley |
| 3,971,383 A | 7/1976 | Van Gerven |
| 4,038,519 A | 7/1977 | Foucras |
| 4,153,048 A | 5/1979 | Magrini |
| 4,160,455 A | 7/1979 | Law |
| 4,190,033 A | 2/1980 | Foti |
| 4,216,767 A | 8/1980 | Aoshiro |
| 4,231,425 A | 11/1980 | Engstrom |
| 4,241,729 A | 12/1980 | Aoshiro |
| 4,275,734 A | 6/1981 | Mitchiner |
| 4,298,006 A | 11/1981 | Parks |
| 4,318,722 A | 3/1982 | Altman |
| 4,323,071 A | 4/1982 | Simpson et al. |
| 4,427,009 A | 1/1984 | Wells et al. |
| 4,445,500 A | 5/1984 | Osterholm |
| 4,464,172 A | 8/1984 | Lichtenstein |
| 4,483,341 A | 11/1984 | Witteles |
| 4,484,586 A | 11/1984 | McMickle et al. |
| 4,502,286 A | 3/1985 | Okada et al. |
| 4,569,355 A | 2/1986 | Bitterly |
| 4,581,017 A | 4/1986 | Sahota |
| 4,602,642 A | 7/1986 | O'Hara et al. |
| 4,655,746 A | 4/1987 | Daniels et al. |
| 4,672,962 A | 6/1987 | Hershenson |
| 4,731,072 A | 3/1988 | Aid |
| 4,739,492 A | 4/1988 | Cochran |
| 4,745,922 A | 5/1988 | Taylor |
| 4,747,826 A | 5/1988 | Sassano |
| 4,748,979 A | 6/1988 | Hershenson |
| 4,750,493 A | 6/1988 | Brader |
| 4,762,129 A | 8/1988 | Bonzel |
| 4,762,130 A | 8/1988 | Fogarty et al. |
| 4,781,799 A | 11/1988 | Herbert, Jr. et al. |
| 4,796,640 A | 1/1989 | Webler |
| 4,817,624 A | 4/1989 | Newbower |
| 4,819,655 A | 4/1989 | Webler |
| 4,820,349 A | 4/1989 | Saab |
| 4,860,744 A | 8/1989 | Johnson et al. |
| 4,883,455 A | 11/1989 | Leonard |
| 4,894,164 A | 1/1990 | Polaschegg |
| 4,904,237 A | 2/1990 | Janese |
| 4,920,963 A | 5/1990 | Brader |
| 4,951,677 A | 8/1990 | Crowlet et al. |
| 4,964,409 A | 10/1990 | Tremulis |
| 4,973,493 A | 11/1990 | Guire |
| 4,979,959 A | 12/1990 | Guire |
| 5,000,734 A | 3/1991 | Boussignac et al. |
| 5,002,531 A | 3/1991 | Bonzel |
| 5,014,695 A | 5/1991 | Benak et al. |
| 5,018,521 A | 5/1991 | Campbell |
| 5,019,075 A | 5/1991 | Spears et al. |
| 5,024,668 A | 6/1991 | Peters et al. |
| 5,041,089 A | 8/1991 | Mueller et al. |
| 5,046,497 A | 9/1991 | Millar |
| 5,059,057 A | 10/1991 | Graef |
| 5,078,713 A | 1/1992 | Varney |
| 5,089,260 A | 2/1992 | Hunter et al. |
| 5,092,841 A | 3/1992 | Spears |
| 5,106,360 A | 4/1992 | Ishwara et al. |
| 5,106,368 A | 4/1992 | Uldall et al. |
| 5,108,390 A | 4/1992 | Potocky et al. |
| RE33,911 E | 5/1992 | Samson et al. |
| 5,110,721 A | 5/1992 | Anaise et al. |
| 5,112,438 A | 5/1992 | Bowers |
| 5,117,822 A | 6/1992 | Laghi |
| 5,139,496 A * | 8/1992 | Hed ............................ 606/23 |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,156,151 A | 10/1992 | Imran |
| 5,180,364 A | 1/1993 | Ginsburg |
| 5,190,539 A | 3/1993 | Fletcher et al. |
| 5,191,883 A | 3/1993 | Lennox et al. |
| 5,196,024 A | 3/1993 | Barath |
| 5,211,631 A | 5/1993 | Sheaff |
| 5,234,405 A | 8/1993 | Klatz et al. |
| 5,236,908 A | 8/1993 | Gruber et al. |
| 5,239,999 A | 8/1993 | Imran |
| 5,246,421 A | 9/1993 | Saab |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,267,341 A | 11/1993 | Shearin |
| 5,269,369 A | 12/1993 | Faghri |
| 5,269,749 A | 12/1993 | Koturov |
| 5,269,758 A | 12/1993 | Taheri |
| 5,279,299 A | 1/1994 | Imran |
| 5,281,213 A | 1/1994 | Milder et al. |
| 5,281,215 A | 1/1994 | Milder |
| 5,306,261 A | 4/1994 | Alliger et al. |
| 5,310,440 A | 5/1994 | Zingher |
| 5,322,514 A | 6/1994 | Steube et al. |
| 5,322,515 A | 6/1994 | Karas et al. |
| 5,322,518 A | 6/1994 | Schneider et al. |
| 5,326,165 A | 7/1994 | Walthall et al. |
| 5,326,166 A | 7/1994 | Walthall et al. |
| 5,330,435 A | 7/1994 | Vaillancourt |
| 5,330,519 A | 7/1994 | Mason et al. |
| 5,334,193 A | 8/1994 | Nardella |
| 5,342,301 A | 8/1994 | Saab |
| 5,342,621 A | 8/1994 | Eury |
| 5,344,436 A | 9/1994 | Fontenot et al. |
| 5,344,740 A | 9/1994 | Iwasawa et al. |
| 5,354,272 A | 10/1994 | Swendson et al. |
| 5,358,486 A | 10/1994 | Saab |
| 5,364,364 A | 11/1994 | Kasvikis et al. |
| 5,365,750 A | 11/1994 | Greenthal |
| 5,368,591 A | 11/1994 | Lennox et al. |
| 5,383,854 A | 1/1995 | Safar et al. |
| 5,383,918 A | 1/1995 | Panetta |
| 5,395,314 A | 3/1995 | Klatz et al. |
| 5,395,331 A | 3/1995 | O'Neill et al. |
| 5,403,281 A | 4/1995 | O'Neill et al. |
| 5,417,686 A | 5/1995 | Peterson et al. |
| 5,423,745 A | 6/1995 | Todd et al. |
| 5,423,807 A | 6/1995 | Milder |
| 5,433,740 A | 7/1995 | Yamaguchi |
| 5,437,673 A | 8/1995 | Baust et al. |
| 5,443,456 A | 8/1995 | Alliger et al. |
| 5,462,521 A | 10/1995 | Brucker et al. |
| 5,486,204 A | 1/1996 | Clifton |
| 5,486,208 A | 1/1996 | Ginsburg |
| 5,496,271 A | 3/1996 | Burton et al. |
| 5,499,973 A | 3/1996 | Saab |
| 5,520,682 A | 5/1996 | Baust et al. |
| 5,531,776 A | 7/1996 | Ward et al. |
| 5,536,247 A | 7/1996 | Thornton |
| 5,545,133 A | 8/1996 | Burns et al. |
| 5,545,708 A | 8/1996 | Onwunaka et al. |
| 5,549,559 A | 8/1996 | Eshel |
| 5,554,119 A | 9/1996 | Harrison et al. |
| 5,558,644 A | 9/1996 | Boyd et al. |
| 5,569,195 A | 10/1996 | Saab |

| Patent No. | Date | Inventor |
|---|---|---|
| 5,573,532 A | 11/1996 | Chang et al. |
| 5,578,008 A | 11/1996 | Hara |
| 5,584,804 A | 12/1996 | Klatz et al. |
| 5,588,438 A | 12/1996 | McKown et al. |
| 5,591,162 A | 1/1997 | Fletcher et al. |
| 5,617,854 A | 4/1997 | Munsif |
| 5,620,480 A | 4/1997 | Rudie |
| 5,622,182 A | 4/1997 | Jaffe |
| 5,624,342 A | 4/1997 | Younger |
| 5,624,392 A | 4/1997 | Saab |
| 5,630,837 A | 5/1997 | Crowley |
| 5,643,197 A | 7/1997 | Brucker et al. |
| 5,647,051 A | 7/1997 | Neer |
| 5,653,692 A | 8/1997 | Masterson et al. |
| 5,676,693 A | 10/1997 | Lafontaine |
| 5,709,654 A | 1/1998 | Klatz et al. |
| 5,713,941 A | 2/1998 | Robins et al. |
| 5,716,386 A | 2/1998 | Ward et al. |
| 5,733,318 A | 3/1998 | Augustine |
| 5,733,319 A | 3/1998 | Neilson et al. |
| 5,735,809 A | 4/1998 | Gorsuch |
| 5,797,878 A | 8/1998 | Bleam |
| 5,799,661 A | 9/1998 | Boyd et al. |
| 5,800,480 A | 9/1998 | Augustine et al. |
| 5,800,483 A | 9/1998 | Vought |
| 5,800,486 A | 9/1998 | Thome |
| 5,800,516 A | 9/1998 | Fine et al. |
| 5,807,391 A | 9/1998 | Wijkamp |
| 5,820,593 A | 10/1998 | Safar et al. |
| 5,824,030 A | 10/1998 | Yang et al. |
| 5,827,222 A | 10/1998 | Klatz et al. |
| 5,827,237 A | 10/1998 | Macoviak et al. |
| 5,827,269 A | 10/1998 | Saadat |
| 5,833,671 A | 11/1998 | Macoviak et al. |
| 5,833,673 A | 11/1998 | Ockuly et al. |
| 5,834,465 A | 11/1998 | Olney |
| 5,837,003 A | 11/1998 | Ginsburg |
| 5,861,021 A | 1/1999 | Thome et al. |
| 5,868,735 A | 2/1999 | Lafontaine |
| 5,871,468 A | 2/1999 | Kramer et al. |
| 5,871,526 A | 2/1999 | Gibbs et al. |
| 5,873,835 A | 2/1999 | Hastings et al. |
| 5,879,316 A | 3/1999 | Safar et al. |
| 5,879,329 A | 3/1999 | Ginsburg |
| 5,891,094 A | 4/1999 | Masterson et al. |
| 5,899,898 A | 5/1999 | Arless et al. |
| 5,899,899 A | 5/1999 | Arless et al. |
| 5,902,268 A | 5/1999 | Saab |
| 5,906,588 A | 5/1999 | Safar et al. |
| 5,906,594 A | 5/1999 | Scarfone et al. |
| 5,906,636 A | 5/1999 | Casscells, III et al. |
| 5,910,104 A | 6/1999 | Dobak, III et al. |
| 5,913,856 A | 6/1999 | Chia et al. |
| 5,913,885 A | 6/1999 | Klatz et al. |
| 5,913,886 A | 6/1999 | Soloman |
| 5,916,242 A | 6/1999 | Schwartz |
| 5,957,917 A | 9/1999 | Doiron et al. |
| 5,957,963 A | 9/1999 | Dobak, III |
| 5,964,751 A | 10/1999 | Amplatz et al. |
| 5,968,009 A | 10/1999 | Siman |
| 5,971,979 A | 10/1999 | Joye et al. |
| 5,989,238 A | 11/1999 | Ginsburg |
| 6,007,692 A | 12/1999 | Herbert et al. |
| 6,011,995 A | 1/2000 | Guglielmi et al. |
| 6,019,783 A | 2/2000 | Philips et al. |
| 6,022,336 A | 2/2000 | Zadno-Azizi et al. |
| 6,024,740 A | 2/2000 | Lesh et al. |
| 6,033,383 A | 3/2000 | Ginsburg |
| 6,042,559 A | 3/2000 | Dobak, III |
| 6,051,019 A | 4/2000 | Dobak, III |
| 6,063,101 A | 5/2000 | Jacobsen et al. |
| 6,096,068 A | 8/2000 | Dobak, III et al. |
| 6,110,168 A | 8/2000 | Ginsburg |
| 6,126,684 A | 10/2000 | Gobin et al. |
| 6,146,411 A | 11/2000 | Noda et al. |
| 6,146,814 A | 11/2000 | Millet |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,165,207 A | 12/2000 | Balding et al. |
| 6,190,354 B1 | 2/2001 | LaFontaine et al. |
| 6,194,899 B1 | 2/2001 | Ishihara et al. |
| 6,224,624 B1 | 5/2001 | Lasheras et al. |
| 6,231,594 B1 | 5/2001 | Dae |
| 6,231,595 B1 | 5/2001 | Dobak, III |
| 6,235,048 B1 | 5/2001 | Dobak, III |
| 6,238,428 B1 | 5/2001 | Werneth et al. |
| 6,245,095 B1 | 6/2001 | Dobak, III et al. |
| 6,251,093 B1 | 6/2001 | Valley et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,264,679 B1 | 7/2001 | Keller et al. |
| 6,277,143 B1 | 8/2001 | Klatz et al. |
| 6,287,326 B1 | 9/2001 | Pecor |
| 6,290,697 B1 | 9/2001 | Tu et al. |
| 6,290,717 B1 | 9/2001 | Philips |
| 6,295,990 B1 | 10/2001 | Lewis et al. |
| 6,299,599 B1 | 10/2001 | Pham et al. |
| 6,306,161 B1 | 10/2001 | Ginsburg |
| 6,312,452 B1 | 11/2001 | Dobak, III et al. |
| 6,315,754 B1 | 11/2001 | Daoud et al. |
| 6,319,248 B1 | 11/2001 | Nahon |
| 6,325,818 B1 | 12/2001 | Werneth |
| 6,336,911 B1 | 1/2002 | Westerbeck |
| 6,338,727 B1 | 1/2002 | Noda et al. |
| 6,354,099 B1 | 3/2002 | Bieberich |
| 6,364,899 B1 | 4/2002 | Dobak, III |
| 6,368,304 B1 | 4/2002 | Aliberto et al. |
| 6,379,378 B1 | 4/2002 | Werneth et al. |
| 6,383,210 B1 | 5/2002 | Magers et al. |
| 6,393,320 B2 | 5/2002 | Lasersohn et al. |
| 6,405,080 B1 | 6/2002 | Lasersohn et al. |
| 6,409,747 B1 | 6/2002 | Gobin et al. |
| 6,416,533 B1 | 7/2002 | Gobin et al. |
| 6,419,643 B1 | 7/2002 | Shimada et al. |
| 6,464,716 B1 | 10/2002 | Dobak, III et al. |
| 6,468,296 B1 | 10/2002 | Dobak, III et al. |
| 6,497,721 B2 | 12/2002 | Ginsburg et al. |
| 6,520,933 B1 | 2/2003 | Evans et al. |
| 6,533,804 B2 * | 3/2003 | Dobak et al. ............. 607/105 |
| 6,540,771 B2 | 4/2003 | Dobak, III |
| 6,544,282 B1 * | 4/2003 | Dae et al. ............. 607/105 |
| 6,641,603 B2 | 11/2003 | Walker et al. |
| 6,648,908 B2 | 11/2003 | Dobak, III |
| 2001/0001830 A1 | 5/2001 | Dobak, III et al. |
| 2001/0001831 A1 | 5/2001 | Dobak, III et al. |
| 2001/0001832 A1 | 5/2001 | Dobak, III et al. |
| 2001/0002442 A1 | 5/2001 | Dobak, III |
| 2001/0005791 A1 | 6/2001 | Ginsburg et al. |
| 2001/0007951 A1 | 7/2001 | Dobak, III |
| 2001/0008975 A1 | 7/2001 | Dobak, III et al. |
| 2001/0010011 A1 | 7/2001 | Aliberto et al. |
| 2001/0011184 A1 | 8/2001 | Dobak, III et al. |
| 2001/0011185 A1 | 8/2001 | Dobak, III et al. |
| 2001/0014802 A1 | 8/2001 | Tu |
| 2001/0016763 A1 | 8/2001 | Lasheras et al. |
| 2001/0016764 A1 | 8/2001 | Dobak, III |
| 2001/0021865 A1 | 9/2001 | Dobak, III et al. |
| 2001/0021866 A1 | 9/2001 | Dobak, III et al. |
| 2001/0029394 A1 | 10/2001 | Dobak, III et al. |
| 2001/0031946 A1 | 10/2001 | Walker et al. |
| 2001/0032003 A1 | 10/2001 | Pecor |
| 2001/0032004 A1 | 10/2001 | Werneth |

| | | | | | | |
|---|---|---|---|---|---|---|
| 2001/0039440 | A1 | 11/2001 | Lasheras et al. | WO | WO 99/66971 | 12/1999 |
| 2001/0041923 | A1 | 11/2001 | Dobak, III | WO | WO 00/09054 | 2/2000 |
| 2001/0044644 | A1 | 11/2001 | Keller et al. | WO | WO 00/47145 | 2/2000 |
| 2001/0047191 | A1 | 11/2001 | Lasersohn et al. | WO | WO 00/10494 | 3/2000 |
| 2001/0047192 | A1 | 11/2001 | Lasersohn et al. | WO | WO 00/38601 | 7/2000 |
| 2001/0047196 | A1 | 11/2001 | Ginsburg | WO | WO 00/48670 | 8/2000 |
| 2001/0049545 | A1 | 12/2001 | Lasersohn et al. | WO | WO 00/51534 | 9/2000 |
| 2002/0002394 | A1 | 1/2002 | Dobak, III | WO | WO 00/53135 | 9/2000 |
| 2002/0004675 | A1 | 1/2002 | Lasheras | WO | WO 00/57823 | 10/2000 |
| 2002/0007179 | A1 | 1/2002 | Dobak, III et al. | WO | WO 00/62837 | 10/2000 |
| 2002/0007202 | A1 | 1/2002 | Dobak, III et al. | WO | WO 00/66053 | 11/2000 |
| 2002/0007203 | A1 | 1/2002 | Gilmartin et al. | WO | WO 00/72779 | 12/2000 |
| 2002/0016621 | A1 | 2/2002 | Werneth et al. | WO | WO 00/72787 | 12/2000 |
| 2002/0022823 | A1 | 2/2002 | Luo et al. | WO | WO 01/03606 | 1/2001 |
| 2002/0026227 | A1 | 2/2002 | Phillips | WO | WO 01/08580 | 2/2001 |
| 2002/0029016 | A1 | 3/2002 | Pham et al. | WO | WO 01/10323 | 2/2001 |
| 2002/0032430 | A1 | 3/2002 | Luo et al. | WO | WO 01/10365 | 2/2001 |
| 2002/0032474 | A1 | 3/2002 | Dobak, III et al. | WO | WO 01/12061 | 2/2001 |
| 2002/0040717 | A1 | 4/2002 | Dobak, III | WO | WO 01/12122 | 2/2001 |
| 2002/0045892 | A1 | 4/2002 | Kramer | WO | WO 01/13809 | 3/2001 |
| 2002/0045925 | A1 | 4/2002 | Keller et al. | WO | WO 01/13837 | 3/2001 |
| 2002/0049409 | A1 | 4/2002 | Noda et al. | WO | WO 01/17471 | 3/2001 |
| 2002/0049410 | A1 | 4/2002 | Noda et al. | WO | WO 01/19447 | 3/2001 |
| 2002/0049484 | A1 | 4/2002 | Werneth et al. | WO | WO 01/26590 | 4/2001 |
| 2002/0056281 | A1 | 5/2002 | Bieberich | WO | WO 01/30413 | 5/2001 |
| 2002/0066458 | A1 | 6/2002 | Aliberto et al. | WO | WO 01/41708 | 6/2001 |
| 2002/0068964 | A1 | 6/2002 | Dobak, III | WO | WO 01/43661 | 6/2001 |
| 2002/0077665 | A1 | 6/2002 | Kordis et al. | WO | WO 01/49236 | 7/2001 |
| 2002/0077680 | A1 | 6/2002 | Noda | WO | WO 01/52781 | 7/2001 |
| 2002/0082671 | A1 | 6/2002 | Magers et al. | WO | WO 01/56517 | 8/2001 |
| 2002/0091378 | A1 | 7/2002 | Dobak, III et al. | WO | WO 01/58397 | 8/2001 |
| 2002/0091429 | A1 | 7/2002 | Dobak, III et al. | WO | WO 01/64145 | 9/2001 |
| 2002/0091430 | A1 | 7/2002 | Dobak, III et al. | WO | WO 01/64146 | 9/2001 |
| 2002/0095200 | A1 | 7/2002 | Dobak, III et al. | WO | WO 01/66052 | 9/2001 |
| 2002/0095201 | A1 | 7/2002 | Worthen et al. | WO | WO 01/74276 | 10/2001 |
| 2002/0138121 | A1 | 9/2002 | Fox | WO | WO 01/76655 | 10/2001 |
| 2002/0151945 | A1 | 10/2002 | Gobin et al. | WO | WO 01/78580 | 10/2001 |
| 2002/0151946 | A1 | 10/2002 | Dobak, III | WO | WO 01/87379 | 11/2001 |
| 2002/0156421 | A1 | 10/2002 | Noda et al. | WO | WO 01/95840 | 12/2001 |
| 2002/0161331 | A1 | 10/2002 | Noda et al. | WO | WO 02/07793 | 1/2002 |
| 2002/0169490 | A1 | 11/2002 | Noda et al. | WO | WO 02/26175 | 4/2002 |
| 2003/0028212 | A1 | 2/2003 | Saab | WO | WO 02/26176 | 4/2002 |
| 2003/0040782 | A1 | 2/2003 | Walker et al. | WO | WO 02/26285 | 4/2002 |
| 2004/0050154 | A1 | 3/2004 | Machold et al. | WO | WO 02/26307 | 4/2002 |
| 2004/0147914 | A1 | 7/2004 | Kramer | WO | WO 02/28300 | 4/2002 |

FOREIGN PATENT DOCUMENTS

| | | | |
|---|---|---|---|
| AU | 734506 B2 | 6/2001 | |
| AU | 739996 B2 | 2/2002 | |
| AU | 743945 B2 | 2/2002 | |
| EP | 0655225 A1 | 5/1993 | |
| EP | 0664990 | 11/1997 | |
| EP | 0428505 B2 | 3/2001 | |
| EP | 1172932 A2 | 7/2001 | |
| EP | 1205167 A2 | 5/2002 | |
| FR | 2 447 406 | 3/1980 | |
| SU | 806 029 | 2/1981 | |
| WO | WO 91/05528 | 5/1991 | |
| WO | WO 93/04727 | 3/1993 | |
| WO | WO 95/01814 | 1/1995 | |
| WO | WO 96/40347 | 12/1996 | |
| WO | WO 97/01374 | 1/1997 | |
| WO | WO 97/25011 | 7/1997 | |
| WO | WO 97/32518 | 9/1997 | |
| WO | WO 98/26831 | 6/1998 | |
| WO | WO 98/31312 | 7/1998 | |
| WO | WO 98/49957 | 11/1998 | |
| WO | WO 99/37226 | 7/1999 | |
| WO | WO 99/44519 | 9/1999 | |
| WO | WO 99/48449 | 9/1999 | |
| WO | WO 99/56812 | 11/1999 | |
| WO | WO 99/66970 | 12/1999 | |

| | | |
|---|---|---|
| WO | WO 02/36180 | 5/2002 |
| WO | WO 02/38091 | 5/2002 |
| WO | WO 02/43577 | 6/2002 |
| WO | WO 02/47577 | 6/2002 |
| WO | WO 02/47742 | 6/2002 |
| WO | WO 02/055129 | 7/2002 |

OTHER PUBLICATIONS

Bigelo; *Hypothermia, Its Possible Role in Cardiac Surgery*; Nov. 1959; pp. 849-866; Annals of Surgery, vol. 132, No. 5.

Cheatle; *Cryostripping the Long and Short Saphenous Veins*; Jan. 1993; one page; Br. J. Surg., vol. 80.

Dexter; *Blood Warms as It Blows Retrograde from a Femoral Cannulation Site to the Carotid Artery During Cardiopulmonary Bypass*; Nov. 1994; pp. 393-397; Perfusion, vol. 9, No. 6.

Gillinov; *Superior Cerebral Protection with Profound Hypothermia During Circulatory Arrest*; Nov. 1992; pp. 1432-1439; Ann. Thorac. Surg., vol. 55.

Higazi; *The Effect of Ultrasonic Irradiation and Temperature on Fibrinolytic Activity in Vitro*; Aug. 1992; p. 251-253; Thrombosis Research, vol. 69, No. 2.

Imamaki; *Retrograde Cerebral Perfusion with Hypothermic Blood Provides Efficient Protection of the Brain*; Jul. 1995; pp. 325-333; Journal of Cardiac Surgery, vol. 10, No. 4, Part 1.

Jolin; *Management of a Giant Intracranial Aneurysm Using Surface-Heparinized Extracorporeal Circulation and Controlled Deep Hypothermic Low Flow Perfusion*; Aug. 1992; pp. 756-760; Acta Anaesthesiologica Scandinavia.

Jos R.C. Jansen, Ph.D., et al. (1997) *Near Continuous Cardiac Output b Thermodilution.* Journal of Clinical Monitoring 13:233-239.

Kimoto; *Open Heart Surgery under Direct Vision with the Aid of Brain-Cooling by Irrigation*; Jul. 1955; pp. 592-603; Surgery, vol. 39, No. 4.

Marekovic, Z.; *Abstract of Renal Hypothermia in Situ by Venous Passages: Experimental Work on Dogs*; 1980; Eur Urol 6(2); 1 page.

Meden; *Effect of Hypothermia and Delayed Thrombolysis in a Rat Embolic Stroke Model*; Dec. 1993; pp. 91-98; Acta Neurologica Scandinavica.

Meden; *The Influence of Body Temperature on Infarct Volume and Thrombolytic Therapy in a Rat Embolic Stroke Model*; Feb. 1994; pp. 131-138; Brain Research, vol. 647.

Milleret, Rene; *La cryo-chirurgie danes les varices des mimbres inferieurs*; Angiologie; Supplement au No. 110.

Milleret; Abstract of *Cryosclerosis of the Saphenous Veins in Varicose Reflux in the Obese and Elderly*; 10.1981; one page; Phlebologie, vol. 34, No. 4.

Parkins; *Brain Cooling in the Prevention of Brain Damage During Periods of Circulatory Occlusion in Dogs*; Apr. 1954; pp. 284-289; Annals of Surgery, vol. 140, No. 3.

Piepgras; *Rapid Active Internal Core Cooling for Induction of Moderate Hypothermia in Head-Injury by Use of an Extracorporeal Heat Exchanger*; Feb. 1998; pp. 311-318; Neurosurgery, vol. 42, No. 2.

Rijken; *Plasminogen Activation at Low Temperatures in Plasma Samples Containing Therapeutic Concentrations of Tissue-Type Plasminogen Activator or Other Thrombolytic Agents*; Oct. 1989; pp. 47-52; place of publication unknown.

Schwartz, A.E. et al.; (1996); *Isolated cerebral hypothermia by single carotid artery perfusion of extracorporeally cooled blood in baboons*; Neurosurgery 39(3):577-582.

Schwartz; *Cerebral Blood Flow during Low-flow Hypothermic Cardiopulmonary Bypass in Baboons*; Jun. 1994; pp. 959-964; Anesthesiology, vol. 81, No. 4.

Schwartz; *Selective Cerebral Hypothermia by Means of Transfemoral Internal Carotid Artery Catheterization*; May 1996; pp. 571-572; Radiology, vol. 201, No. 2.

Steen; *The Detrimental Effects of Prolonged Hypothermia and Rewarming in the Dog*; Aug. 1979; pp. 224-230; Anesthesiology, vol. 52, No. 3.

Vandam; *Hypothermia*; Sep. 1959; pp. 546-553; The New England Journal of Medicine.

White; *Cerebral Hypothermia and Circulatory Arrest*; Jul. 1978; pp. 450-458; Mayo Clinic Proceedings, vol. 53.

Yenari; *Thrombolysis with Tissue Plasminogen Activator (TPA) is Temperature Dependent*; Jul. 1994; pp. 475-481; Thrombosis Research, vol. 77, No. 5.

Yoshihara; *Changes in Coagulation and Fibrinolysis Occurring in Dogs during Hypothermia*; Aug. 1984; pp. 503-512; Thrombosis Research, vol. 37, No. 4.

Zarins; *Circulation in Profound Hypothermia*; Nov. 1972; pp. 97-104; Journal of Surgical Research, vol. 14, N. 2.

Colvett, K. T. et al. "Opportunities with Combined Modality Therapy for Selective Organ Preservation in Muscle-Invasive Bladder Cancer," May 1996, *Journ. Surg. Oncology* 63:202-201.

Mass, C. et al. "Intermittent Antegrade/Selective Cerebral Perfusion during Circulatory Arrest for Repair of the Aortic Arch," 1997, *Perfusion*, 12:127-132.

Alfonsi, P., D. I. Sessler, B. Du Manoir, J-C. Levron, J-P. Le Moing, M. Chauvin, *The Effects of Meperidine and Sufentanil on the Shivering Threshold in Postoperative Patients*, Anesthesiology, Jul. 1998, 89(1):43-48.

Anon, "Automatic feedback instrumentation for hospital room utilizing microsensors," *IBM Technical Disclosure Bulletin (ABS.)*, 29(3): 1 page, Aug. 1986.

Benzinger, T.H.; *On Physical Heart Regulation and Sense of Temperature in Man*; Naval Medical Research Institute; Physiology; vol. 45; pp. 645-659; (Feb. 26, 1959).

Brengelmann, George L.; *Specialized Brain Cooling in Humans?*; The FASEB Journal; vol. 7; pp. 1148-1153 (Sep. 1993).

Buggy, D., P. Higgins, C. Moran, F. O'Donovan, and M. McCarroll, *Clonidine at Induction Reduces Shivering after General Anaesthesia*, 1997, pp. 263-267, Can. J. Anaesth., vol. 44, N. 3.

Cabanac, M., *Selective Brain Cooling and Thermoregulatory Set-Point*, 1998, pp. 3-13, Journ. of Basic & Clinical Physiology & Pharmacology, vol. 9, N. 1.

Cabanac, M.; *Selective Brain Cooling in Humans: fancy or fact?*; The FASEB Journal; vol. 7; pp. 1143-1147 (Sep. 1993).

Capogna, G. and D. Celleno, *I. V. Clonidine for Post-Extradural Shivering in Parturients: A Preliminary Study*, 1993, Brit. Journ. of Anaesth., vol. 71.

Carrol et al. "A comparison of measurements from a temporal artery thermometer and a pulmonary artery thermistor—preliminary results." Fax Correspondence dated Oct. 19, 2001.

Cheng, C. , T. Matsukawa, D. I. Sessler, M. Ozaki, A. Kurz, B. Merrifield, L. Hank, and P. Olofsson, *Increasing Mean Skin Temperature Linearly Reduces the Core-Temperature Thresholds for Vasoconstriction and Shivering in Humans*, May 1995, pp. 1160-1168, Anesthesiology, vol. 82, N. 5.

De Ford et al. "Design and evaluation of closed-loop feedback control of minimum temperatures in human intracranial tumours treated with interstitial hyperthermia," Med. & Biol. Eng. & Comput. 29:197-206, Mark 1991.

Deklunder, G., M. Dauzat, J-L. Lecroart, J-J. Hauser, and Y. Houdas, "Influence of Ventilation of the Face on Thermoregulation in Man during Hyper- and Hypothermia," *Eur. J. Appl. Physiol.*, 1991,62:342-348.

Gentilello, L. M., "Advances in the Management of Hypothermia," *Horizons in Trauma Surgery*, 75(2)243-256, Apr. 1995.

Giesbrecht, G. G., M. S.. L. Goheen, C. E. Johnston, G. P. Kenny, G. K. Bristow, and J. S. Hayward, *Inhibition of Shivering Increases Core Temperature Afterdrop and Attenuates Rewarming in Hypothermic Humans*, 1997, 0161-7567:1630-1634, The American Physiological Society.

Giuffre, M., J. Finnie, D. A. Lynam, and D. Smith, *Rewarming Postoperative Patients: Lights, Blankets, or Forced Warm Air*, Dec. 1991, pp. 387-393, Journ. of Post Anaesthesia Nursing, vol. 6, N. 6.

Guffin, A., D. Girard, and J. A. Kaplan, *Shivering Following Cardiac Surgery: Hemodynamic Changes and Reversal*, Feb. 1987, pp. 24-28, Journ. of Cardiothoracic Anesthesia, vol. 1, N. 1.

Haley, E. C. et al. "A Randomized Trial of Tirilazad Mesylate in Patients with Acute Stroke (RANTTAS)," *Stroke*, 27(9):1453-1458, 1996.

Iaizzo, *Facial Warming Increases the Threshold for Shivering*, 1999; pp. 231-239, Journ. of Neurosurgical Anesthesiology, vol. 11, No. 4.

Keegan, M. T. et al. *Shivering Complicating the Treatment of Neurologically Impaired Surgical and Intensive Care Unit Patients*, Anesthesiology, 91(3):874-876, Sep. 1999.

Kogaku "Sensor technology to control artificial organs," KLA, 22(4):295-300, Aug. 1984 (in Japanese).

Kurz, Martin, et al.; "Naloxone, Meperidine, and Shivering."; *Anesthesiology*; 79 (6):1193-1201; Dec. 1993.

Lennon, R. L., M. P. Hosking, M. A. Conover, and W. J. Perkins, *Evaluation of a Forced-Air System for Warming Hypothermic Postoperative Patients*, 1990, pp. 424-427, Anesth. Analg., vol. 70.

Leslie, K., D. I. Sessler, A. R. Bjorksten, M. Ozaki, T. Matsukawa, and M. Schroeder, *Propofol Causes a Dose-Dependent Decrease in the Thermoregulatory Threshold for vasoconstriction but has Little Effect on Sweating*, Aug. 1994, pp. 353-360, vol. 81, N. 2.

Matsukawa, T., A. Kurz, D. I. Sessler, A. R. Bjorksten, B. Merrifield, and C. Cheng, *Propofol Linearly Reduces the Vasoconstriction and Shivering Thresholds*, May 1995, pp. 1169-1180, Anesthesiology, vol. 82, N. 5.

Meden, P., K. Overgaard, H. Pedersen, G. Boysen, *Effect of Hypothermia and Delayed Thrombolysis in a Rat Embolic Stroke Model*, 1994, pp. 91-98, Acta Neurol. Scand. vol. 90.

Möller et al. "Temperature control and light penetration in a feedback interstitial laser thermotherapy system," *Int. J. Hyperthermia*, 12(1):49-63, 1996.

Olshausen et al. "An isothermal flowmeter with improved frequency response for measuring tissue blood flow," Pflügers Arch, 367:97-102, 1976.

Pais, S. O., K. D. Tobin, C. B. Austin, and L. Queral, *Percutaneous Insertion of the Greenfield Inferior Vena Cava Filter: Experience with Ninety-Six Patients*, Oct. 1988, pp. 460-464, Journ. of Vascular Surg., vol. 8, N. 4.

Patton, J. H, T. C. Fabian, M. A. Croce, G. Minard, F. E. Pritchard, and K. A. Kudsk, *Prophylactic Greenfield Filters: Acute Complications and Long-Term Follow-Up*, Aug. 1996; pp. 231-237; Journ. of Trauma: Injury, Infection, and Critical Care, vol. 41, N.2.

Rohrer, M. J. and A. M. Natale, *Effect of Hypothermia on the Coagulation Cascade*, Oct. 1992, pp. 1402-1405, Critical Care Medicine, vol. 20, N. 10.

Schmid-Elsaesser, R. et al. (1999), *Combination Drug Therapy and Mild Hypothermia: A Promising Treatment Strategy for Reversible, Focal Cerebral Ischemia*, Stroke, 1891-1899, June.

Sessler, Daniel I.; "Mild Perioperative Hypothermia"; The New England Journal of Medicine; 336:1730-1737; Jun. 12, 1997.

Sharkey, A., J. M. Lipton, M. T. Murphy, and A. H. Giesecke, *Inhibition of Postanesthestic Shivering with Radiant Heat*, Feb. 1987, pp. 249-252, Anesthesiology, vol. 66, N. 2.

Shiraki, K., N. Konda, and S. Sagawa, Esphageal and Tympanic Temperature Responses to Core Blood Temperature Changes during Hyperthermia, *J. Appl. Physiol*. 61(1):98-102 (1986).

Simon, M., C. A. Athanasoulis, D. Kim, F. L. Steinberg, D. H Porter, B. H. Byse, S. Kleshinski, S. Geller, D. E. Orron, and A. C. Waltman; *Simon Nitinol Inferior Vena Cava Filter: Initial Clinical Experience*, Jul. 1989, pp. 99-103; Radiology.

Villamaria, F. J., C. E. Baisden, A. Hillis, M. H. Rajab, and P. A. Rinaldi, "Forced-Air Warming is No More Effective than Conventional Methods for Raising Postoperative Core Temperature After Cardiac Surgery," *Journ. Cardiothoracic and Vascular Anesth.*, 11(6):708-711, Oct. 1997.

Zweifler, R. M. and D. I. Sessler, "Thermoregulatory Vasoconstriction and Shivering Impede Therapeutic Hypothermia in Acute Ischemic Stroke Patients," *Journ. Stroke and Cerebrovascular Diseases*, 6(2):100-104, 1996.

Schwartz, Arthur E., et al.; Isolated Cerebral Hypothermia by Single Carotid Artery Perfusion of Extracorporeally Cooled Blood in Baboons ; Neurosurgery, vol. 39, No. 3, pp. 577-582 (Sep. 1996).

Hederer, G., et al.; "Animal Experiment Observations Regarding Cardiac Surgery under Intravascular Hypothermia"; Labgebbecjs Arch. U. Dtsch. A. Chir., Bd. 283, S. 601-625 (1957) (German article with English translation).

Behmann, F.W; "Heat Generation Control during Artificial Hypothermia: II. Theoretical Examinations"; Pflügers Archiv, Bd. 266, S. 422-446 (1958) (German article with English translation).

Behmann, F.W., et al.; <<Heat Generation Control during Artificial Hypothermia: I: Experimental Examination of the Influence of Anesthetic Depth; Pflügers Archiv, Bd. 266, S. 408-421 (1958) (German article with English translation).

Behmann, F.W., et al.; Intravascular Cooling, a Method to Achieve Controllable Hypothermia; Pflügers Archive, vol. 263, pp. 145-165 (1956) (German article with English translation).

Behmann, F.W.; "Heat Generation Control during Artificial Hypothermia, an article about the economic problem of trembling stages"; Pflügers Archive, vol. 263, pp. 166-187 (1956) (German article with English translation).

Behmann, F.W.; "Regulation of heat production in experimental hypothermia of homothermal animals"; Naunyn Schmiedebergs Arch Exp Pathol.Pharmakol; 228 (1-2): 126-128 (1956). (German article with English translation).

* cited by examiner

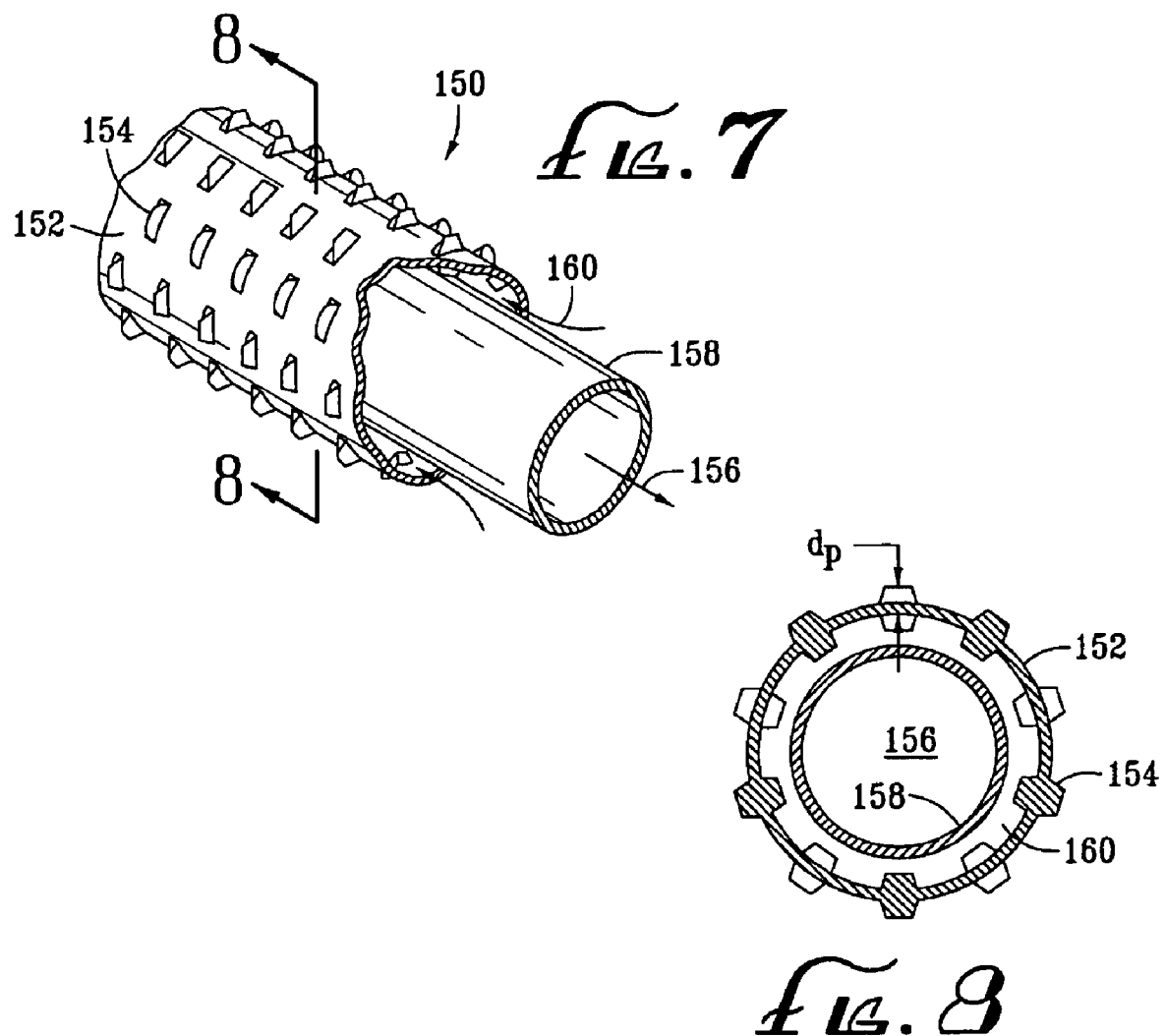

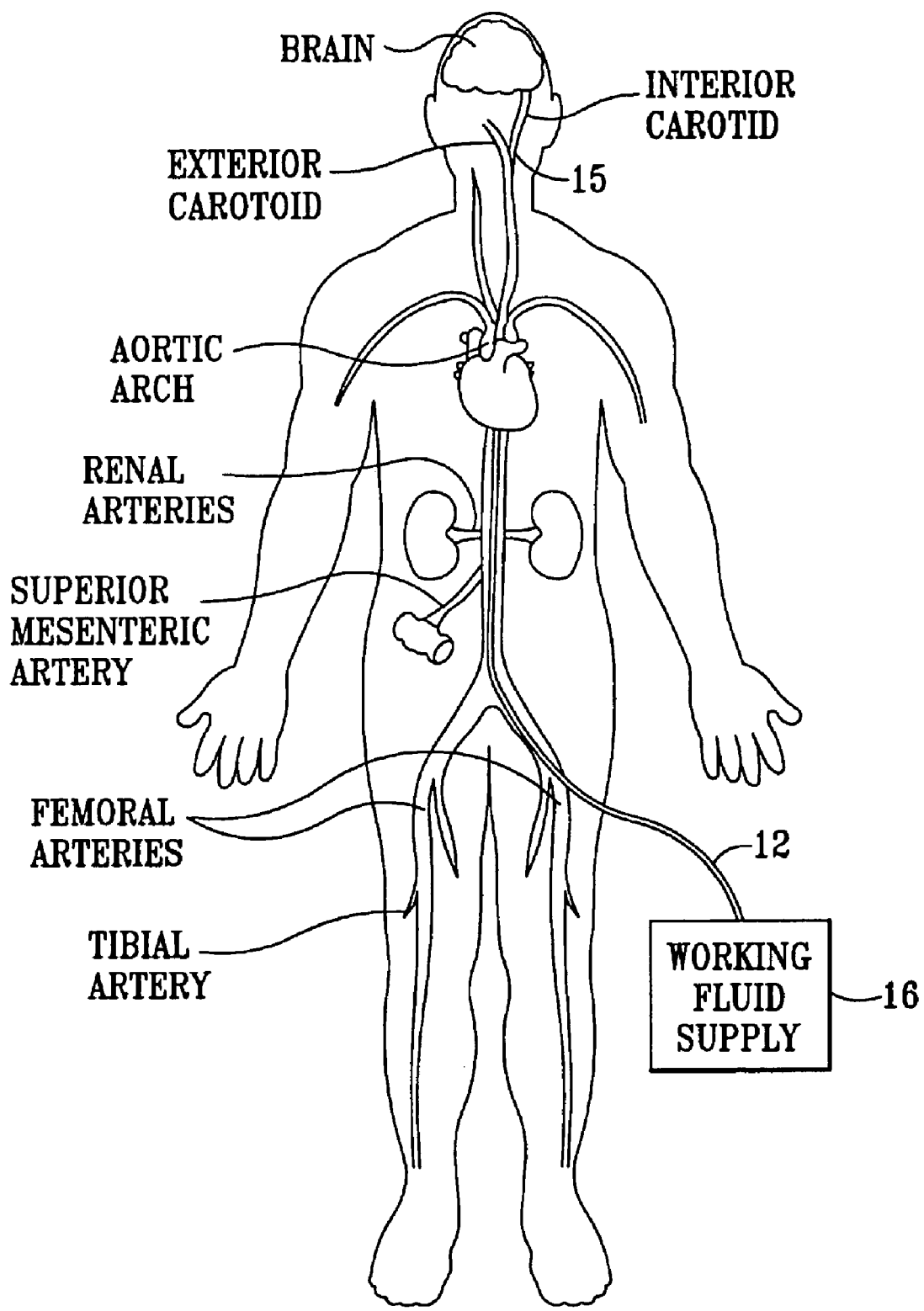

INFLATABLE CATHETER FOR SELECTIVE ORGAN HEATING AND COOLING AND METHOD OF USING THE SAME

CROSS REFERENCE TO RELATED APPLICATIONS

This is a continuation application of U.S. patent application Ser. No. 10/095,753, filed on Mar. 11, 2002, entitled "Inflatable Catheter For Selective Organ Heating And Cooling And Method Of Using The Same", now U.S. Pat. No. 6,695,873, which is a divisional patent application of U.S. patent application Ser. No. 09/757,124, filed on Jan. 8, 2001, entitled "Inflatable Catheter For Selective Organ Heating And Cooling And Method Of Using The Same ", now U.S. Pat. No. 6,540,771, which is a divisional of U.S. patent application Ser. No. 09/215,038 filed on Dec. 16, 1998, entitled "Inflatable Catheter For Selective Organ Heating And Cooling And Method Of Using The Same", now U.S. Pat. No. 6,261,312, which is a continuation-in-part of U.S. patent application Ser. No. 09/103,342 filed on Jun. 23, 1998, entitled "Selective Organ Cooling Catheter And Method Of Using Same", now U.S. Pat. No. 6,096,068, which is a continuation-in-part of U.S. patent. application Ser. No. 09/047,012 filed on Mar. 24, 1998, entitled "Selective Organ Hypothermia Method And Apparatus" now U.S. Pat. No. 5,957,963, which is a continuation-in-part of U.S. patent application Ser. No. 09/012,287 filed on Jan. 23, 1998, entitled "Selective Organ Hypothermia Method And Apparatus", now U.S. Pat. No. 6,051,019, all of which are incorporated herein.

STATEMENT REGARDING FEDERALLY SPONSORED RESEARCH OR DEVELOPMENT

Not Applicable

BACKGROUND OF THE INVENTION

1. Field of the Invention

The invention relates generally to the modification and control of the temperature of a selected body organ. More particularly, the invention relates to a method and intravascular apparatus for controlling organ temperature.

2. Background Information

Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Hypothermia is uniquely effective in reducing brain injury caused by a variety of neurological insults and may eventually play an important role in emergency brain resuscitation. Experimental evidence has demonstrated that cerebral cooling improves the patient's outcome after global ischemia, focal ischemia, or traumatic brain injury. For this reason, hypothermia may be induced in order to reduce the effect of certain bodily injuries to the brain as well as other organs.

Cerebral hypothermia has traditionally been accomplished through whole body cooling to create a condition of total body hypothermia in the range of 20° C. to 30° C. However, the use of total body hypothermia risks certain deleterious systematic vascular effects. For example, total body hypothermia may cause severe derangement of the cardiovascular system, including low cardiac output, elevated systematic resistance, and ventricular fibrillation. Other side effects include renal failure, disseminated intravascular coagulation, and electrolyte disturbances. In addition to the undesirable side effects, total body hypothermia is difficult to administer.

Catheters have been developed which are inserted into the bloodstream of the patient in order to induce total body hypothermia. For example, U.S. Pat. No. 3,425,419 to Dato describes a device and technique of lowering and raising the temperature of the human body. The Dato reference discloses a technique of inducing moderate hypothermia in a patient using a metallic catheter. The metallic catheter has an inner passageway through which a fluid, such as water, can be circulated. The catheter is inserted through the femoral vein and then through the inferior vena cava as far as the right atrium and the superior vena cava. The Dato reference discloses a catheter having an elongated cylindrical shape and is constructed from stainless steel. By way of example, Dato suggests the use of a catheter approximately 70 cm in length and approximately 6 mm in diameter. However, use of the Dato device implicates the negative effects of total body hypothermia described above.

Due to the problems associated with total body hypothermia, attempts have been made to provide more selective cooling. For example, cooling helmets or head gear have been used in an attempt to cool only the head rather than the patient's entire body. However, such methods rely on conductive heat transfer through the skull and into the brain. One drawback of using conductive heat transfer is that the process of reducing the temperature of the brain is prolonged. Also, it is difficult to precisely control the temperature of the brain when using conduction due to the temperature gradient that must be established externally in order to sufficiently lower the internal temperature. In addition, when using conduction to cool the brain, the face of the patient is also subjected to severe hypothermia, increasing discomfort and the likelihood of negative side effects. It is known that profound cooling of the face can cause similar cardiovascular side effects as total body cooling. From a practical standpoint, such devices are cumbersome and may make continued treatment of the patient difficult or impossible.

Selective organ hypothermia has also been attempted by perfusion of a cold solution such as saline or perflourocarbons. This process is commonly used to protect the heart during heart surgery and is referred to as cardioplegia. Perfusion of a cold solution has a number of drawbacks, including a limited time of administration due to excessive volume accumulation, cost, and inconvenience of maintaining the perfusate and lack of effectiveness due to the temperature dilution from the blood. Temperature dilution by the blood is a particular problem in high blood flow organs such as the brain.

Therefore, there is a need for a practical method and apparatus which modifies and controls the temperature of a selected organ but does not suffer from the drawbacks of total body hypothermia or cold perfusion.

BRIEF SUMMARY OF THE INVENTION

The invention provides a method and device to transfer heat to or from a selected organ in an efficient manner. The device has a high degree of lateral flexibility and is collapsible, thereby affording an easy insertion procedure. The device allows high surface area to increase heat transfer.

In one aspect, the invention is directed to a catheter system to change the temperature of blood by heat transfer to or from a working fluid. The system includes an inflatable inlet lumen and outlet lumen. The outlet lumen is coupled to the inlet lumen so as to transfer working fluid between the two. The outlet lumen has a structure when inflated to induce turbulence in the blood and/or in the working fluid.

Variations of the system may include one or more of the following. The inlet lumen and the outlet lumen may be made of a flexible material such as latex rubber. The outlet lumen may have a structure to induce turbulence in the working fluid when inflated, such as a helical shape which may be tapered in a segmented or non-segmented manner. The radii of the inlet and outlet lumens may decrease in a distal direction such that the inlet and outlet lumens are tapered when inflated. A wire may be disposed in the inlet or outlet lumens to provide shape and strength when deflated.

The thickness of the outlet lumen, when inflated, may be less than about ½ mil. The length of the inlet lumen may be between about 5 and 30 centimeters. If the outlet lumen has a helical shape, the diameter of the helix may be less than about 8 millimeters when inflated. The outer diameter of the helix of the outlet lumen, when inflated, may be between about 2 millimeters and 8 millimeters and may taper to between about 1 millimeter and 2 millimeters. In segmented embodiments, a length of a segment may be between about 1 centimeter and 10 centimeters. The radii of the inlet and outlet lumens when inflated may be between about 0.5 millimeters and 2 millimeters.

The outlet lumen may further include at least one surface feature and/or interior feature, the surface feature inducing turbulence in the fluid adjacent the outlet lumen and the interior feature inducing turbulence in the working fluid. The surface feature may include one or more helical turns or spirals formed in the outlet lumen. Adjacent turns may employ opposite helicity. Alternatively or in combination, the surface feature may be a series of staggered protrusions formed in the outlet lumen.

The turbulence-inducing outlet lumen may be adapted to induce turbulence when inflated within a free stream of blood when placed within an artery. The turbulence intensity may be greater than about 0.05. The turbulence-inducing outlet lumen may be adapted to induce turbulence when inflated throughout the period of the cardiac cycle when placed within an artery or during at least 20% of the period.

The system may further include a coaxial supply catheter having an inner catheter lumen coupled to the inlet lumen and a working fluid supply configured to dispense the working fluid and having an output coupled to the inner catheter lumen. The working fluid supply may be configured to produce a pressurized working fluid at a temperature of between about −3° C. and 36° C. and at a pressure below about 5 atmospheres of pressure. Higher temperatures may be employed if blood heating is desired.

The turbulence-inducing outlet lumen may include a surface coating or treatment such as heparin to inhibit clot formation. A stent may be coupled to the distal end of the inlet lumen. The system may be employed to cool or heat volumes of tissue rather than blood.

In embodiments employing a tapered helical outlet lumen, the taper of the outlet lumen allows the outlet lumen to be placed in an artery having a radius less than the first radius. The outlet lumen may be tapered in segments. The segments may be separated by joints, the joints having a radius less than that of either adjacent segment.

In another aspect, the invention is directed to a method of changing the temperature of blood by heat transfer. The method includes inserting an inflatable heat transfer element into an artery or vein and inflating the same by delivering a working fluid to its interior. The temperature of the working fluid is generally different from that of the blood. The method further includes inducing turbulence in the working fluid by passing the working fluid through a turbulence-inducing path, such that turbulence is induced in a substantial portion of a free stream of blood. The inflatable heat transfer element may have a turbulence-inducing structure when inflated.

In another aspect, the invention is directed towards a method of treating the brain which includes inserting a flexible heat transfer element into an artery from a distal location and circulating a working fluid through the flexible heat transfer element to inflate the same and to selectively modify the temperature of an organ without significantly modifying the temperature of the entire body. The flexible, conductive heat transfer element preferably absorbs more than about 25, 50 or 75 watts of heat. The artery may be the common carotid or a combination of the common carotid and the internal carotid.

In another aspect, the invention is directed towards a method for selectively cooling an organ in the body of a patient which includes introducing a catheter into a blood vessel supplying the organ, the catheter having a diameter of 5 mm or less, inducing free stream turbulence in blood flowing over the catheter, and cooling the catheter to remove heat from the blood to cool the organ without substantially cooling the entire body. In one embodiment, the cooling removes at least about 75 watts of heat from the blood. In another embodiment, the cooling removes at least about 100 watts of heat from the blood. The organ being cooled may be the human brain.

The circulating may further include passing the working fluid in through an inlet lumen and out through an outlet, coaxial lumen. The working fluid may be a liquid at or well below its boiling point, and furthermore may may be aqueous.

Advantages of the invention include one or more of the following. The design criteria described above for the heat transfer element: small diameter when deflated, large diameter when inflated, high flexibility, and enhanced heat transfer rate through increases in the surface of the heat transfer element and the creation of turbulent flow, facilitate creation of a heat transfer element which successfully achieves selective organ cooling or heating. Because only a selected organ is cooled, complications associated with total body hypothermia are avoided. Because the blood is cooled intravascularly, or in situ, problems associated with external circulation of the blood are eliminated. Also, only a single puncture and arterial vessel cannulation are required which may be performed at an easily accessible artery such as the femoral, subclavian, or brachial arteries. By eliminating the use of a cold perfusate, problems associated with excessive fluid accumulation are avoided. In addition, rapid cooling to a precise temperature may be achieved. Further, treatment of a patient is not cumbersome and the patient may easily receive continued care during the heat transfer process. The device and method may be easily combined with other devices and techniques to provide aggressive multiple therapies. Other advantages will become clear from the description below.

The novel features of this invention, as well as the invention itself, will be best understood from the attached drawings, taken along with the following description, in which similar reference characters refer to similar parts, and in which:

BRIEF DESCRIPTION OF THE SEVERAL
VIEWS OF THE DRAWINGS

The features, objects, and advantages of the invention will become more apparent from the detailed description set forth below when taken in conjunction with the drawings in which like reference characters identify corresponding elements throughout.

In FIG. 6 a spiral feature is shown.

FIG. 7 illustrates another type of turbulence-inducing surface feature which may be employed in the heat transfer element of the embodiment of FIG. 5. In FIG. 7, a series of staggered protrusions are shown.

FIG. 8 is a transverse cross-sectional view of the heat transfer element of the embodiment of FIG. 7.

FIG. 10 is a schematic representation of an embodiment of the invention being used to cool the brain of a patient.

DETAILED DESCRIPTION OF THE INVENTION

The temperature of a selected organ may be intravascularly regulated by a heat transfer element placed in the organ's feeding artery to absorb or deliver heat to or from the blood flowing into the organ. While the device is described with respect to blood flow into an organ, it is understood that heat transfer within a volume of tissue is analogous. In the latter case, heat transfer is predominantly by conduction.

The heat transfer may cause either a cooling or a heating of the selected organ. A heat transfer element that selectively alters the temperature of an organ should be capable of providing the necessary heat transfer rate to produce the desired cooling or heating effect within the organ to achieve a desired temperature.

The heat transfer element should be small and flexible enough to fit within the feeding artery while still allowing a sufficient blood flow to reach the organ in order to avoid ischemic organ damage. Feeding arteries, like the carotid artery, branch off the aorta at various levels. Subsidiary arteries continue to branch off these initial branches. For example, the internal carotid artery branches off the common carotid artery near the angle of the jaw. The heat transfer element is typically inserted into a peripheral artery, such as the femoral artery, using a guide catheter or guide wire, and accesses a feeding artery by initially passing though a series of one or more of these branches. Thus, the flexibility and size, e.g., the diameter, of the heat transfer element are important characteristics. This flexibility is achieved as is described in more detail below.

These points are illustrated using brain cooling as an example. The common carotid artery supplies blood to the head and brain. The internal carotid artery branches off the common carotid artery to supply blood to the anterior cerebrum. The heat transfer element according to the principles of the invention may be placed into the common carotid artery or into both the common carotid artery and the internal carotid artery.

The benefits of hypothermia described above are achieved when the temperature of the blood flowing to the brain is reduced to between 30° C. and 32° C. A typical brain has a blood flow rate through each carotid artery (right and left) of approximately 250-375 cubic centimeters per minute (cc/min). With this flow rate, calculations show that the heat transfer element should absorb approximately 75-175 watts of heat when placed in one of the carotid arteries to induce the desired cooling effect. Smaller organs may have less blood flow in their respective supply arteries and may require less heat transfer, such as about 25 watts.

Figure 1:
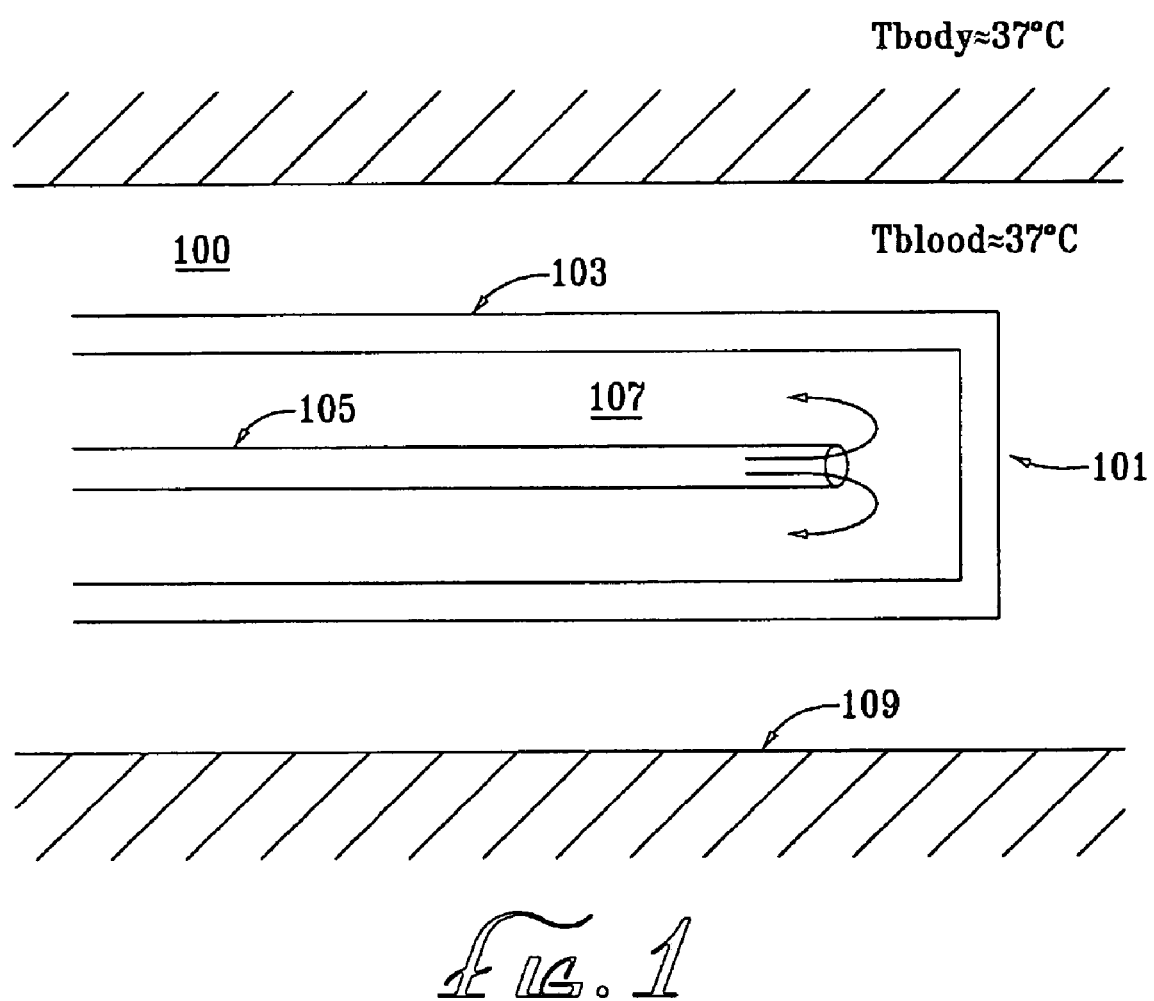
FIG. 1 is a schematic diagram of a heat transfer element according to an embodiment of the invention.

A device according to an embodiment of the invention for accomplishing such cooling or heating is shown schematically in FIG. 1, which shows an arterial wall 109 in which a blood flow 100 is passing. A catheter 101 is disposed within the blood flow 100 to affect the blood temperature. Catheter 101 has an inlet lumen 105 for providing a working fluid 107 and an outlet lumen 103 for draining the working fluid 107. The functions of the respective lumens may of course be opposite to that stated. A reverse configuration may be particularly advantageous when blood heating, rather than blood cooling, is the objective.

Heat transfer in this system is governed by the following mechanisms:
(1) convective heat transfer from the blood 100 to the outlet lumen 103;
(2) conduction through the wall of the outlet lumen 103;
(3) convective heat transfer from the outlet lumen 103 to the working fluid 107;
(4) conduction through the working fluid 107;
(5) convective heat transfer from working fluid 107 in the outlet lumen 103 to the inlet lumen 105; and
(6) conduction through the wall of the inlet lumen 105.

Once the materials for the lumens and the working fluid are chosen, the conductive heat transfers are solely dependent on the temperature gradients. Convective heat transfers, by contrast, also rely on the movement of fluid to transfer heat. Forced convection results when the heat transfer surface is in contact with a fluid whose motion is induced (or forced) by a pressure gradient, area variation, or other such force. In the case of arterial flow, the beating heart provides an oscillatory pressure gradient to force the motion of the blood in contact with the heat transfer surface. One of the aspects of the device uses turbulence to enhance this forced convective heat transfer.

The rate of convective heat transfer Q is proportional to the product of S, the area of the heat transfer element in direct contact with the fluid, $\Delta T = T_b - T_s$, the temperature differential between the surface temperature $T_s$ of the heat transfer element and the free stream blood temperature $T_b$, and $\overline{h}_c$, the average convection heat transfer coefficient over the heat transfer area. $\overline{h}_c$ is sometimes called the "surface coefficient of heat transfer" or the "convection heat transfer coefficient".

The magnitude of the heat transfer rate Q to or from the fluid flow can be increased through manipulation of the above three parameters. Practical constraints limit the value of these parameters and how much they can be manipulated. For example, the internal diameter of the common carotid artery ranges from 6 to 8 mm. Thus, the heat transfer element residing therein may not be much larger than 4 mm in diameter to avoid occluding the vessel. The length of the heat transfer element should also be limited. For placement within the internal and common carotid artery, the length of the heat transfer element is limited to about 10 cm. This estimate is based on the length of the common carotid artery, which ranges from 8 to 12 cm.

Consequently, the value of the surface area S is limited by the physical constraints imposed by the size of the artery into which the device is placed. Surface features, such as fins, can be used to increase the surface area of the heat transfer element, however, these features alone cannot provide enough surface area enhancement to meet the required heat transfer rate to effectively cool the brain. An embodiment of the device described below provides a tapered heat transfer element which employs a large surface area but which may advantageously fit into small arteries. As the device is inflatable, the same may be inserted in relatively small arteries in a deflated state, allowing a minimally invasive entry. When the device is in position, the same may be inflated, allowing a large surface area and thus an enhanced heat transfer rate.

One may also attempt to vary the magnitude of the heat transfer rate by varying $\Delta T$. The value of $\Delta T = T_b - T_s$ can be varied by varying the surface temperature $T_s$ of the heat transfer element. The allowable surface temperature of the heat transfer element is limited by the characteristics of blood. The blood temperature is fixed at about 37° C., and blood freezes at approximately 0° C. When the blood approaches freezing, ice emboli may form in the blood which may lodge downstream, causing serious ischemic injury. Furthermore, reducing the temperature of the blood also increases its viscosity which results in a small decrease in the value of $\overline{h}_c$. Increased viscosity of the blood may further result in an increase in the pressure drop within the artery, thus compromising the flow of blood to the brain. Given the above constraints, it is advantageous to limit the surface temperature of the heat transfer element to approximately 1° C.-5° C., thus resulting in a maximum temperature differential between the blood stream and the heat transfer element of approximately 32° C.-36° C.

One may also attempt to vary the magnitude of the heat transfer rate by varying $\overline{h}_c$. Fewer constraints are imposed on the value of the convection heat transfer coefficient $\overline{h}_c$. The mechanisms by which the value of $\overline{h}_c$ may be increased are complex. However, one way to increase $\overline{h}_c$ for a fixed mean value of the velocity is to increase the level of turbulent kinetic energy in the fluid flow.

The heat transfer rate $Q_{no-flow}$ in the absence of fluid flow is proportional to $\Delta T$, the temperature differential between the surface temperature $T_s$ of the heat transfer element and the free stream blood temperature $T_b$ times k, the diffusion constant, and is inversely proportion to $\delta$, the thickness of the boundary layer.

The magnitude of the enhancement in heat transfer by fluid flow can be estimated by taking the ratio of the heat transfer rate with fluid flow to the heat transfer rate in the absence of fluid flow $N = Q_{flow}/Q_{no-flow} = \overline{h}_c/(k/\delta)$. This ratio is called the Nusselt number ("Nu"). For convective heat transfer between blood and the surface of the heat transfer element, Nusselt numbers of 30-80 have been found to be appropriate for selective cooling applications of various organs in the human body. Nusselt numbers are generally dependent on several other numbers: the Reynolds number, the Womersley number, and the Prandtl number.

Stirring-type mechanisms, which abruptly change the direction of velocity vectors, may be utilized to induce turbulent kinetic energy and increase the heat transfer rate. The level of turbulence so created is characterized by the turbulence intensity $\theta$. Turbulence intensity $\theta$ is defined as the root mean square of the fluctuating velocity divided by the mean velocity. Such mechanisms can create high levels of turbulence intensity in the free stream, thereby increasing the heat transfer rate. This turbulence intensity should ideally be sustained for a significant portion of the cardiac cycle, and should ideally be created throughout the free stream and not just in the boundary layer.

Turbulence does occur for a short period in the cardiac cycle anyway. In particular, the blood flow is turbulent during a small portion of the descending systolic flow. This portion is less than 20% of the period of the cardiac cycle. If a heat transfer element is placed co-axially inside the artery, the heat transfer rate will be enhanced during this short interval. For typical of these fluctuations, the turbulence intensity is at least 0.05. In other words, the instantaneous velocity fluctuations deviate from the mean velocity by at least 5%. Although ideally turbulence is created throughout the entire period of the cardiac cycle, the benefits of turbulence are obtained if the turbulence is sustained for 75%, 50% or even as low as 30% or 20% of the cardiac cycle.

One type of turbulence-inducing heat transfer element which may be advantageously employed to provide heating or cooling of an organ or volume is described in co-pending U.S. patent application Ser. No. 09/103,342 to Dobak and Lasheras for a "Selective Organ Cooling Catheter and Method of Using the Same," incorporated by reference above. In that application, the heat transfer element is made of a high thermal conductivity material, such as metal. The metal heat transfer element provides a high degree of heat transfer due to its high thermal conductivity. In that application, bellows provided a high degree of articulation that compensated for the intrinsic stiffness of the metal. The device size was minimized, e.g., less than 4 mm, to prevent blockage of the blood flowing in the artery.

On the other hand, the heat transfer element according to an embodiment of the present invention is made of a flexible material, such as latex rubber. The latex rubber provides a high degree of flexibility which was previously achieved by articulation. The latex rubber further allows the heat transfer element to be made collapsible so that when deflated the same may be easily inserted into an artery. Insertion and location may be conveniently made by way of a guide catheter or guide wire. Following insertion and location in the desired artery, the heat transfer element may be inflated for use by a working fluid such as saline, water, perfluorocarbons, or other suitable fluids.

A heat transfer element made of a flexible material generally has significantly less thermal conductivity than a heat transfer element made of metal. The device compensates for this by enhancing the surface area available for heat transfer. This may be accomplished in two ways: by increasing the cross-sectional size and by increasing the length. Regarding the former, the device may be structured to be large when inflated, because when deflated the same may still be inserted into an artery. In fact, the device may be as large as the arterial wall, so long as a path for blood flow is allowed, because the flexibility of the device tends to prevent damage to the arterial wall even upon contact. Such paths are described below. Regarding the latter, the device may be configured to be long. One way to configure a long device is to taper the same so that the device may fit into distal arteries having reduced radii in a manner described below. The device further compensates for the reduced thermal conductivity by reducing the thickness of the heat transfer element wall.

Embodiments of the device use a heat transfer element design that produces a high level of turbulence in the free stream of the blood and in the working fluid. One embodiment of the invention forces a helical motion on the working fluid and imposes a helical barrier in the blood, causing turbulence. In an alternative embodiment, the helical barrier is tapered. In a second alternative embodiment, a tapered inflatable heat transfer element has surface features to cause turbulence. As one example, the surface features may have a spiral shape. In another example, the surface features may be staggered protrusions. In all of these embodiments, the design forces a high level of turbulence in the free stream of the blood by causing the blood to navigate a tortuous path while passing through the artery. This tortuous path causes the blood to undergo violent accelerations resulting in turbulence.

In a third alternative embodiment of the invention, a taper of an inflatable heat transfer element provides enough additional surface area per se to cause sufficient heat transfer. In all of the embodiments, the inflation is performed by the working fluid, such as water or saline.

Figure 2:
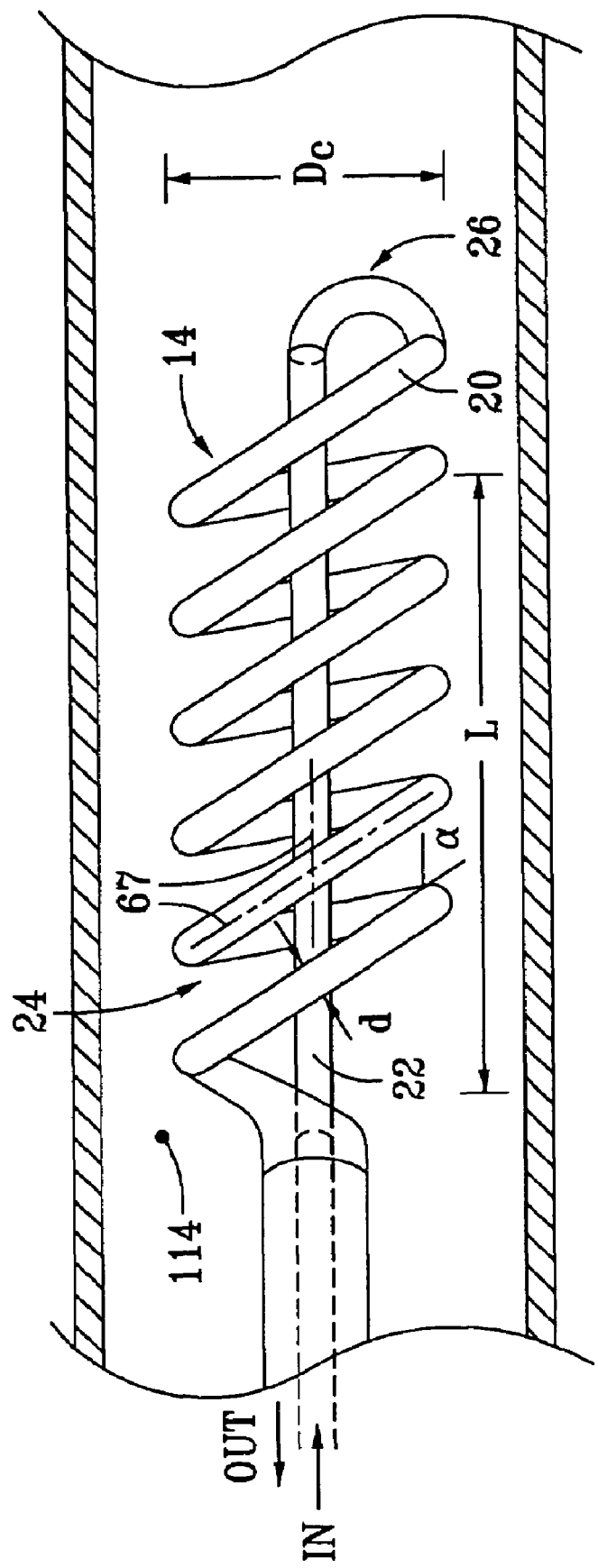
FIG. 2 is a side schematic view of an inflatable turbulence-inducing heat transfer element according to an embodiment of the invention, as the same is disposed within an artery.

Referring to FIG. 2, a side view is shown of a first embodiment of a heat transfer element 14 according to an embodiment of the invention. The heat transfer element 14 is formed by an inlet lumen 22 and an outlet lumen 20. In this embodiment, the outlet lumen 20 is formed in a helix shape surrounding the inlet lumen 22 that is formed in a pipe shape. The names of the lumens are of course not limiting. It will be clear to one skilled in the art that the inlet lumen 22 may serve as an outlet and the outlet lumen 20 may serve as an inlet. It will also be clear that the heat transfer element is capable of both heating (by delivering heat to) and cooling (by removing heat from) a desired area.

The heat transfer element 14 is rigid but flexible so as to be insertable in an appropriate vessel by use of a guide catheter. Alternatively, the heat transfer element may employ a device for threading a guide wire therethrough to assist placement within an artery. The heat transfer element 14 has an inflated length of L, a helical diameter of $D_c$, a tubal diameter of d, and a helical angle of $\alpha$. For example, $D_c$ may be about 3.3 mm and d may be about 0.9 mm to 1 mm. Of course, the tubal diameter d need not be constant. For example, the diameter of the inlet lumen 22 may differ from that of the outlet lumen 14.

The shape of the outlet lumen 20 in FIG. 2 is helical. This helical shape presents a cylindrical obstacle, in cross-section, to the flow of blood. Such obstacles tend to create turbulence in the free stream of blood. In particular, the form of turbulence is the creation of von Karman vortices in the wake of the flow of blood, downstream of the cylindrical obstacles.

Typical inflatable materials are not highly thermally conductive. They are much less conductive than the metallic heat transfer element disclosed in the patent application incorporated by reference above. The difference in conductivity is compensated for in at least two ways in the present device. The material is made thinner and the heat transfer element is afforded a larger surface area. Regarding the former, the thickness may be less than about ½ mil for adequate cooling.

Thin inflatable materials, particularly those with large surface areas, may require a structure, such as a wire, within their interiors to maintain their approximate uninflated positions so that upon inflation, the proper form is achieved. Thus, a wire structure 67 is shown in FIG. 2 which may be advantageously disposed within the inflatable material to perform such a function.

Another consideration is the angle $\alpha$ of the helix. Angle $\alpha$ should be determined to optimize the helical motion of the blood around the lumens 20 and 22, enhancing heat transfer. Of course, angle $\alpha$ should also be determined to optimize the helical motion of the working fluid within the lumens 20 and 22. The helical motion of the working fluid within the lumens 20 and 22 increases the turbulence in the working fluid by creating secondary motions. In particular, helical motion of a fluid in a pipe induces two counter-rotating secondary flows.

An enhancement of $\overline{h_c}$ would be obtained in this system, and this enhancement may be described by a Nusselt number Nu of up to about 10 or even more.

Figure 3:
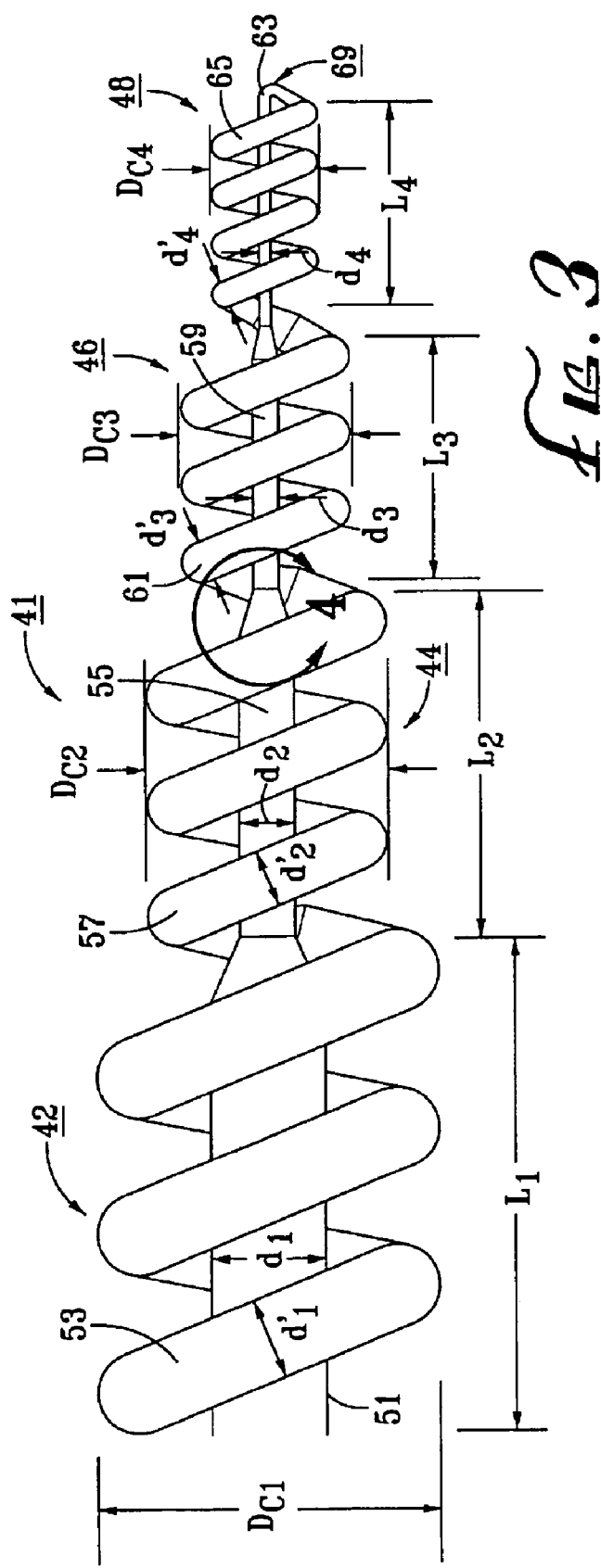
FIG. 3 illustrates an inflatable turbulence-inducing heat transfer element according to an alternative embodiment of the invention employing a surface area enhancing taper and a turbulence-inducing shape.

The above discussion describes one embodiment of a heat transfer element. An alternative embodiment of the device, shown in a side view in FIG. 3, illustrates a heat transfer element 41 with a surface area enhancement. Increasing the surface area of the inflatable material enhances heat transfer. The heat transfer element 14 includes a series of coils or helices of different coil diameters and tubal diameters. It is not strictly necessary that the tubal diameters differ, but it is likely that commercially realizable systems will have differing tubal diameters. The heat transfer element 14 may taper either continuously or segmentally.

This alternative embodiment enhances surface area in two ways. First, the use of smaller diameter lumens enhances the overall surface-to-volume ratio. Second, the use of progressively smaller (i.e., tapered) lumens allows a distal end 69 to be inserted further into an artery than would be possible with the embodiment of FIG. 2.

In the embodiment of FIG. 3, a first coil segment 42 is shown having length $L_1$ and diameter $D_{C1}$. The first coil segment 42 is formed of an inlet lumen 51 having diameter $d_1$ and an outlet lumen 53 having diameter $d_1'$. In the first coil segment, as well as the others, the outlet lumen need not immediately drain the inlet lumen. In FIG. 3, the inlet lumen for each segment feeds the inlet lumen of the succeeding segment except for an inlet lumen adjacent a distal end 69 of the heat transfer element 41 which directly feeds its corresponding outlet lumen.

A separate embodiment may also be constructed in which the inlet lumens each provide working fluid to their corresponding outlet lumens. In this embodiment, either a separate lumen needs to be provided to drain each outlet lumen or each outlet lumen drains into the adjacent outlet lumen. This embodiment has the advantage that an opposite helicity may be accorded each successive segment. The opposite helicities in turn enhance the turbulence of the working fluid flowing past them.

A second coil segment 44 is shown having length $L_2$ and diameter $D_{C2}$. The second coil segment 44 is formed of an inlet lumen 55 having diameter $d_2$ and an outlet lumen 57 having diameter $d_2'$. A third coil segment 46 is shown having length $L_3$ and diameter $D_{C3}$. The third coil segment 46 is formed of an inlet lumen 59 having diameter $d_3$ and an outlet lumen 61 having diameter $d_3'$. Likewise, a fourth coil segment 48 is shown having length $L_4$ and diameter $D_{C4}$. The fourth coil segment 48 is formed of an inlet lumen 63 having diameter $d_4$ and an outlet lumen 65 having diameter $d_4'$. The diameters of the lumens, especially that of the lumen located at or near distal end 69, should be large enough to not restrict the flow of the working fluid within them. Of course, any number of lumens may be provided depending on the requirements of the user.

Figure 4:
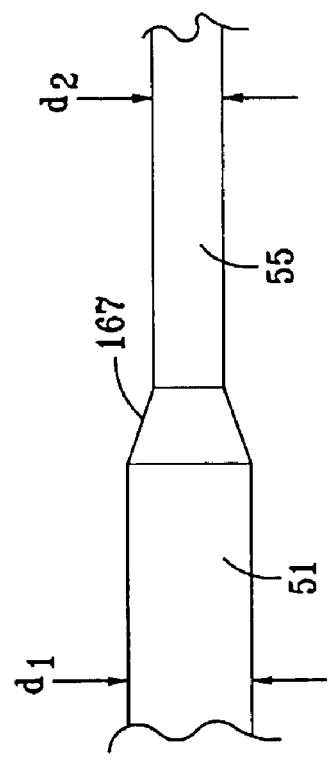
FIG. 4 illustrates a tapered joint which may be employed in the embodiment of FIG. 3.

FIG. 4 shows the connection between two adjacent inlet lumens 51 and 55. A joint 167 is shown coupling the two lumens. The construction of the joint may be by way of variations in stress, hardening, etc.

An advantage to this alternative embodiment arises from the smaller diameters of the distal segments. The heat transfer element of FIG. 3 may be placed in smaller workspaces than the heat transfer element of FIG. 2. For example, a treatment for brain trauma may include placement of a cooling device in the internal carotid artery of a patient. As noted above, the common carotid artery feeds the internal carotid artery. In some patients, the heat transfer element of FIG. 2 may not fit in the internal carotid artery. Similarly, the first coil segment of the heat transfer element in FIG. 3 may not easily fit in the internal carotid artery, although the second, third, and fourth segments may fit. Thus, in the embodiment of FIG. 3, the first coil segment may remain in the common carotid artery while the segments of smaller diameter (the second, third, and fourth) may be placed in the internal carotid artery. In fact, in this embodiment, $D_{C1}$ may be large, such as 5-6 mm. The overall length of the heat transfer element 41 may be, e.g., about 20 to 25 cm.

An additional advantage was mentioned above. The surface area of the alternative embodiment of FIG. 3 may be substantially larger than that of the embodiment of FIG. 2, resulting in significantly enhanced heat transfer. For example, the enhancement in surface area may be substantial, such as up to or even more than three times compared to the surface area of the device of the application incorporated by reference above. An additional advantage of both embodiments is that the helical rounded shape allows atraumatic insertion into cylindrical cavities such as, e.g., arteries.

The embodiment of FIG. 3 may result in an Nu from 1 up to about 50.

Figure 5:
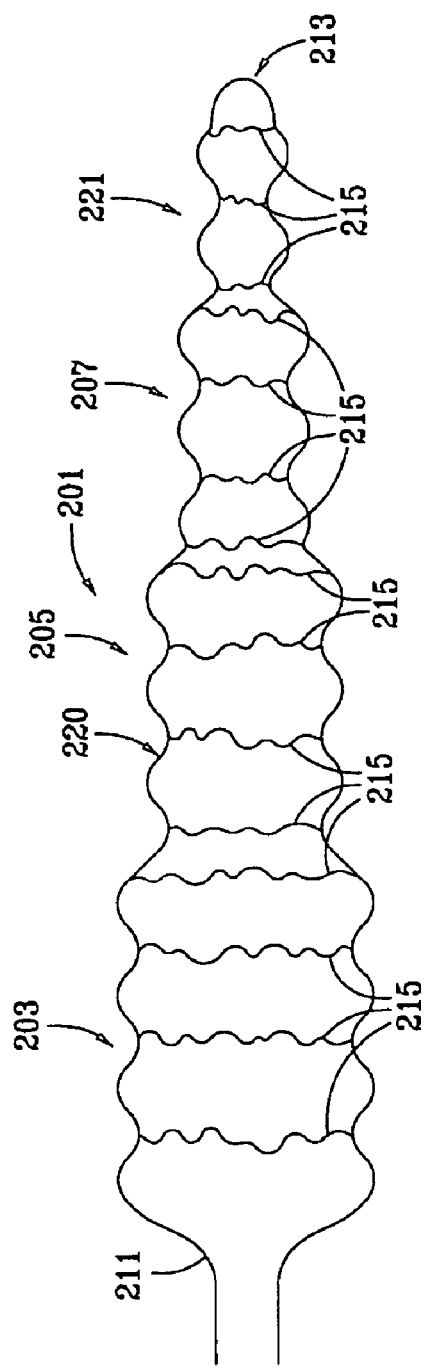
FIG. 5 illustrates a turbulence-inducing heat transfer element according to a second alternative embodiment of the invention employing a surface area enhancing taper and turbulence-inducing surface features.

FIG. 5 shows a second alternative embodiment of the device employing surface features rather than overall shape to induce turbulence. In particular, FIG. 5 shows a heat transfer element 201 having an inlet lumen (not shown) and an outlet inflatable lumen 220 having four segments 203, 205, 207, and 221. Segment 203 is adjacent a proximal end 211 and segment 221 is adjacent a distal end 213. The segments are arranged having reducing radii in the direction of the proximal end to the distal end. In a manner similar to that of the embodiment of FIG. 3, the feature of reducing radii allows insertion of the heat transfer element into small work places such as small arteries.

Figure 6:
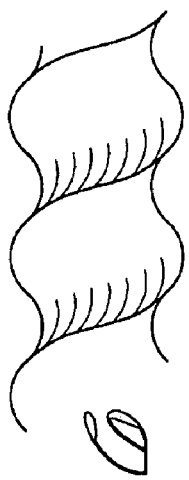
FIG. 6 illustrates a type of turbulence-inducing surface feature which may be employed in the heat transfer element of the embodiment of FIG. 5.

Heat transfer element 201 has a number of surface features 215 disposed thereon. The surface features 215 may be constructed with, e.g., various hardening treatments applied to the heat transfer element 201, or alternatively by injection molding. The hardening treatments may result in a wavy or corrugated surface to the exterior of heat transfer element 201. The hardening treatments may further result in a wavy or corrugated surface to the interior of heat transfer element 201. FIG. 6 shows a variation of this embodiment, in which a fabrication process is used which results in a spiral or helical shape to the surface features.

The embodiment of FIG. 5 may result in an Nu of about 1 to 50.

In another variation of this embodiment, shown in FIG. 7, a heat transfer element 150 employs a plurality of protrusions 154 on outlet lumen 152 which surrounds an inlet lumen 158. In particular, FIG. 7 is a cut-away perspective view of an alternative embodiment of a heat transfer element 150. A working fluid is circulated through an inlet lumen 156 to a distal tip of the heat transfer element 150 thereby inflating the heat transfer element 150. The working fluid then traverses an outlet coaxial lumen 160 in order to transfer heat from the exterior surface 152 of the heat transfer element 150. The inside structure of the heat transfer element 150 is similar to the exterior structure in order to induce turbulent flow of the working fluid.

An external surface 152 of the inflatable heat transfer element 150 is covered with a series of staggered protrusions 154. The staggered nature of the protrusions 154 is readily seen with reference to FIG. 8 which is a transverse cross-sectional view of an inflated heat transfer element taken along the line 8-8 in FIG. 7. In order to induce free stream turbulence, the height, $d_p$, of the staggered protrusions 154 is greater than the thickness of the boundary layer which would develop if a smooth heat transfer element had been introduced into the blood stream. As the blood flows along the external surface 152, it collides with one of the staggered protrusions 154 and a turbulent flow is created. As the blood divides and swirls along side of the first staggered protrusion 154, it collides with another staggered protrusion 154 within its path preventing the re-lamination of the flow and creating yet more turbulence. In this way, the velocity vectors are randomized and free stream turbulence is created. As is the case with the other embodiments, this geometry also induces a turbulent effect on the internal coolant flow.

The embodiment of FIG. 7 may result in an Nu of about 1 to 50.

Of course, other surface features may also be used which result in turbulence in fluids flowing past them. These include spirals, helices, protrusions, various polygonal bodies, pyramids, tetrahedrons, wedges, etc.

Figure 9:
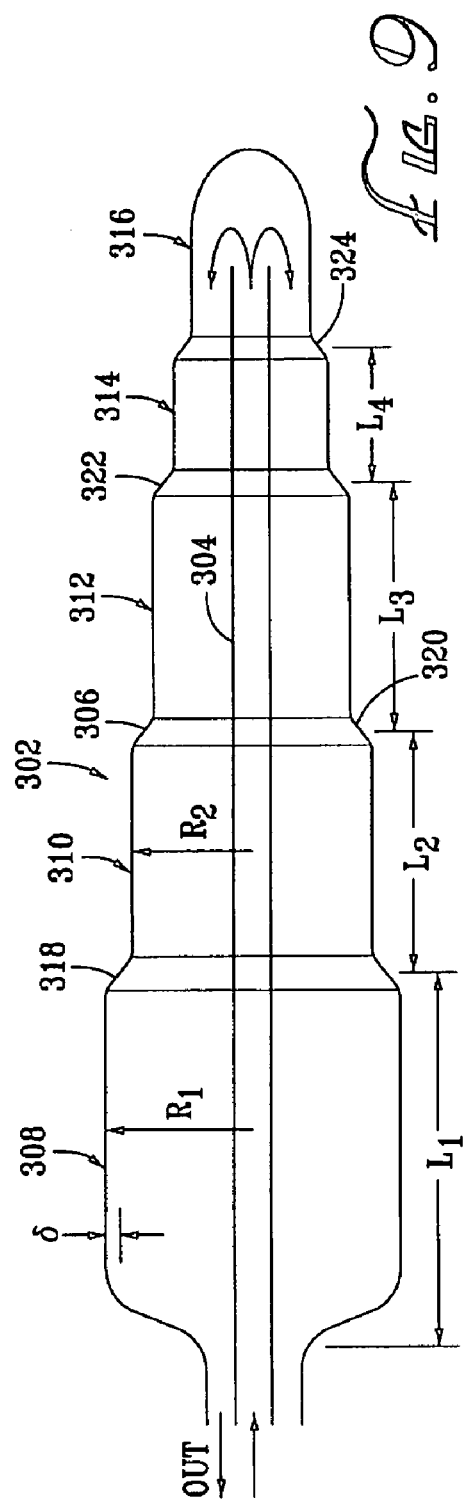
FIG. 9 illustrates a heat transfer element according to a third alternative embodiment of the invention employing a surface area enhancing taper.

In some situations, an enhanced surface area alone, without the creation of additional turbulence, may result in sufficient heat transfer to cool the blood. Referring to FIG. 9, a heat transfer element 302 is shown having an inlet lumen 304 and an outlet lumen 306. The inlet lumen 304 provides a working fluid to the heat transfer element 302 and outlet lumen 306 drains the working fluid from the same. The functions may, of course, be reversed. The heat transfer element 302 is further divided into five segments, although more or less may be provided as dictated by requirements of the user. The five segments in FIG. 9 are denoted segments 308, 310, 312, 314, and 316. In FIG. 9, the segment 308 has a first and largest radius $R_1$, followed by corresponding radii for segments 310, 312, 314, and 316. Segment 316 has a second and smallest radius. The length of the segment 308 is $L_1$, followed by corresponding lengths for segments 310, 312, 314, and 316.

A purely tapered (nonsegmented) form may replace the tapered segmental form, but the former may be more difficult to manufacture. In either case, the tapered form allows the heat transfer element 302 to be disposed in small arteries, i.e., arteries with radii smaller than $R_1$. A sufficient surface area is thus afforded even in very small arteries to provide the required heat transfer.

The surface area and thus the size of the device should be substantial to provide the necessary heat transfer. Example dimensions for a three-segmented tapered form may be as follows: $L_1=10$ cm, $R_1=2.5$ mm; $L_2=10$ cm, $R_2=1.65$ mm, $L_3=5$ cm, $R_3=1$ mm. Such a heat transfer element would have an overall length of 25 cm and a surface area of $3 \times 10^{-4}$ m$^2$.

The embodiment of FIG. 9 results in an enhancement of the heat transfer rate of up to about 300% due to the increased surface area S alone.

A variation of the embodiment of FIG. 9 includes placing at least one turbulence-inducing surface feature within the interior of the outlet lumen 306. This surface feature may induce turbulence in the working fluid, thereby increasing the convective heat transfer rate in the manner described above.

Another variation of the embodiment of FIG. 9 involves reducing the joint diameter between segments (not shown). For example, the inflatable material may be formed such that joints 318, 320, 322, and 324 have a diameter only slightly greater than that of the inlet lumen 304. In other words, the heat transfer element 302 has a tapered "sausage" shape.

In all of the embodiments, the inflatable material may be formed from seamless and nonporous materials which are therefore impermeable to gas. Impermeability can be particularly important depending on the type of working fluid which is cycled through the heat transfer element. For example, the inflatable material may be latex or other such rubber materials, or alternatively of any other material with similar properties under inflation. The flexible material allows the heat transfer element to bend, extend and compress so that it is more readily able to navigate through tiny blood vessels. The material also provides for axial compression of the heat transfer element which can limit the trauma when the distal end of the heat transfer element 14 abuts a blood vessel wall. The material should be chosen to tolerate temperatures in the range of −1° C. to 37° C., or even higher in the case of blood heating, without a loss of performance.

It may be desirable to treat the surface of the heat transfer element to avoid clot formation because the heat transfer element may dwell within the blood vessel for extended periods of time, such as 24-48 hours or even longer. One means by which to prevent thrombus formation is to bind an antithrombogenic agent to the surface of the heat transfer element. For example, heparin is known to inhibit clot formation and is also known to be useful as a biocoating.

Referring back to FIG. 2, an embodiment of the method of the invention will be described. A description with reference to the embodiment of FIG. 3 is analogous. A guide catheter or wire may be disposed up to or near the area to be cooled or heated. The case of a guide catheter will be discussed here. The heat transfer element may be fed through the guide catheter to the area. Alternatively, the heat transfer element may form a portion of the guide catheter. A portion of the interior of the guide catheter may form, e.g., the return lumen for the working fluid. In any case, the movement of the heat transfer element is made significantly more convenient by the flexibility of the heat transfer element as has been described above.

Once the heat transfer element 14 is in place, a working fluid such as saline or other aqueous solution may be circulated through the heat transfer element 14 to inflate the same. Fluid flows from a supply catheter into the inlet lumen 22. At the distal end 26 of the heat transfer element 14, the working fluid exits the inlet lumen 22 and enters the outlet lumen 20.

In the case of the embodiment of FIG. 5, for which the description of FIG. 7 is analogous, the working fluid exits the inlet lumen and enters an outlet inflatable lumen 220 having segments 203, 205, 207, and 221. As the working fluid flows through the outlet lumen 220, heat is transferred from the exterior surface of the heat transfer element 201 to the working fluid. The temperature of the external surface may reach very close to the temperature of the working fluid because the heat transfer element 201 is constructed from very thin material.

The working fluids that may be employed in the device include water, saline or other fluids which remain liquid at the temperatures used. Other coolants, such as freon, undergo nucleated boiling and may create turbulence through a different mechanism. Saline is a safe coolant because it is non-toxic and leakage of saline does not result in a gas embolism which may occur with the use of boiling refrigerants.

By enhancing turbulence in the coolant, the coolant can be delivered to the heat transfer element at a warmer temperature and still achieve the necessary heat transfer rate. In particular, the enhanced heat transfer characteristics of the internal structure allow the working fluid to be delivered to the heat transfer element at lower flow rates and lower pressures. This is advantageous because high pressures may stiffen the heat transfer element and cause the same to push against the wall of the vessel, thereby shielding part of the heat transfer unit from the blood. Such pressures are unlikely to damage the walls of the vessel because of the increased flexibility of the inflated device. The increased heat transfer characteristics allow the pressure of the working fluid to be delivered at pressures as low as 5 atmospheres, 3 atmospheres, 2 atmospheres or even less than 1 atmosphere.

In a preferred embodiment, the heat transfer element creates a turbulence intensity greater than 0.05 in order to create the desired level of turbulence in the entire blood stream during the whole cardiac cycle. The turbulence intensity may be greater than 0.055, 0.06, 0.07 or up to 0.10 or 0.20 or even greater.

FIG. 10 is a schematic representation of the device being used to cool the brain of a patient. The selective organ hypothermia apparatus includes a working fluid supply 16, preferably supplying a chilled liquid such as water, alcohol or a halogenated hydrocarbon, a supply catheter 12 and the heat transfer element 15. The heat transfer element 15 may have the form, e.g., of any of the embodiments above or of similar such heat transfer elements. The supply catheter 12 has a coaxial construction. An inlet lumen within the supply catheter 12 receives coolant from the working fluid supply 16. The coolant travels the length of the supply catheter 12 to the heat transfer element 15 which serves as the cooling tip of the catheter. At the distal end of the heat transfer element 15, the coolant exits the insulated interior lumen and traverses the length of the heat transfer element 15 in order to decrease the temperature of the heat transfer element 15. The coolant then traverses an outlet lumen of the supply catheter 12, which may have a helical or other shape as described above. The supply catheter 12 is a flexible catheter having a diameter sufficiently small to allow its distal end to be inserted percutaneously into an accessible artery such as the femoral artery of a patient. The supply catheter 12 is sufficiently long to allow the heat transfer element 15 to be passed through the vascular system of the patient and placed in the internal carotid artery or other small artery. If the heat transfer element 15 employs tapering as in some of the embodiments described above, the same may be placed in very small arteries without damage to the arterial walls.

The heat transfer element can absorb or provide over 75 watts of heat to the blood stream and may absorb or provide as much as 100 watts, 150 watts, 170 watts or more. For example, a heat transfer element with a diameter of 4 mm and a length of approximately 10 cm, using ordinary saline solution chilled so that the surface temperature of the heat transfer element is approximately 5° C. and pressurized at 2 atmospheres, can absorb about 150 watts of energy from the bloodstream. Smaller geometry heat transfer elements may be developed for use with smaller organs which provide 60 watts, 50 watts, 25 watts or less of heat transfer.

The practice of the invention is illustrated in the following non-limiting example.

Exemplary Procedure

1. The patient is initially assessed, resuscitated, and stabilized.
2. The procedure is carried out in an angiography suite or surgical suite equipped with fluoroscopy.
3. Because the catheter is placed into the common carotid artery, it is important to determine the presence of stenotic atheromatous lesions. A carotid duplex (Doppler/ultrasound) scan can quickly and non-invasively make this determination. The ideal location for placement of the catheter is in the left carotid. Thus, the same may be scanned first. If disease is present, then the right carotid artery can be assessed. This test can be used to detect the presence of proximal common carotid lesions by observing the slope of the systolic upstroke and the shape of the pulsation. Although these lesions are rare, they could inhibit the placement of the catheter. Examination of the peak blood flow velocities in the internal carotid can determine the presence of internal carotid artery lesions. Although the catheter is placed proximally to such lesions, the catheter may exacerbate the compromised blood flow created by these lesions. Peak systolic velocities greater that 130 cm/sec and peak diastolic velocities>100 cm/sec in the internal carotid indicate the presence of at least 70% stenosis. Stenosis of 70% or more may warrant the placement of a stent to open up the internal artery diameter.

4. Ultrasound can also be used to determine the vessel diameter and the blood flow. A catheter with an appropriately-sized heat transfer element could be selected.
5. After assessment of the arteries, the patient's inguinal region is sterilely prepped and infiltrated with lidocaine.
6. The femoral artery is cannulated and a guide wire may be inserted to the desired carotid artery. Placement of the guide wire is confirmed with fluoroscopy.
7. An angiographic catheter can be fed over the wire and contrast media injected into the artery to further assess the anatomy of the carotid.
8. Alternatively, the femoral artery is cannulated and a 10-12.5 french (f) introducer sheath is placed.
9. A guide catheter may be placed into the desired common carotid artery. If a guide catheter is placed, it can be used to deliver contrast media directly to further assess carotid anatomy.
10. The 10 f -12 f (3.3-4.0 mm) (approximate) heat transfer device is then prepared.
11. The heat transfer device and supply catheter are placed into the carotid artery via the guiding catheter or over the guidewire. Placement is confirmed with fluoroscopy. This placement is conveniently made in part because of the flexibility of the heat transfer element.
12. Alternatively, the catheter tip is shaped (angled or curved approximately 45 degrees), and the catheter shaft has sufficient pushability and torqueability to be placed in the carotid without the aid of a guide wire or guide catheter. Such pushability and torqueability may be achieved with the use of a wire placed within the catheter shaft and heat transfer element.
13. If cooling is desired, the catheter according to the invention is connected to a pump circuit also filled with saline and free from air bubbles. The pump circuit has a heat exchange section that is immersed into a water bath and tubing that is connected to a peristaltic pump. The water bath is chilled to approximately 0° C.
14. Cooling is initiated by starting the pump mechanism. The saline within the cooling catheter is circulated at 5 cc/sec. The saline travels through the heat exchanger in the chilled water bath and is cooled to approximately 1° C.
15. The saline subsequently enters the cooling catheter where it is delivered to the heat transfer element. The saline is warmed to approximately 5-7° C. as it travels along the inlet lumen of the catheter shaft to the end of the heat transfer element.
16. The saline then flows back through the heat transfer element in contact with the outlet lumen. The saline is further warmed in the heat transfer element to 12-15° C., and in the process, heat is absorbed from the blood, cooling the blood to 30° C. to 32° C.
17. The chilled blood then chills the brain. 15-30 minutes may be required to cool the brain to 30 to 32° C.
18. The warmed saline travels back down the outlet lumen of the catheter shaft and back to the chilled water bath where it is cooled to 1° C.
19. The pressure drops along the length of the circuit are estimated to be 2-3 atmospheres.
20. The cooling can be adjusted by increasing or decreasing the flow rate of the saline. Monitoring the temperature drop of the saline along the heat transfer element will allow the flow to be adjusted to maintain the desired cooling effect.
21. The catheter may be left in place to provide cooling for 12 to 24 hours.
22. If desired, warm saline can be circulated to promote warming of the brain at the end of the therapeutic cooling period.

In addition, in some applications, it may be advantageous to attach a stent to the distal end of the heat transfer element. The stent may be used to open arteries partially obstructed by atheromatous disease prior to initiation of heat transfer. Further, the device may be used to deliver drugs such as blood clot dissolving compounds (e.g., tissue plasminogen activator ("tPA"), urokinase, pro-urokinase, streptokinase, etc.) or neuroprotective agents (e.g., selective neurotransmitter inhibitors). In addition to therapeutic uses, the device may be used to destroy tissue such as through cryosurgery.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A catheter system to change the temperature of blood by heat transfer to or from a circulating working fluid, comprising:
 an inlet lumen to introduce a circulating working fluid; and
 at least one outlet lumen to extract a circulating working fluid, the outlet lumen having a structure disposed within the outlet lumen to maintain its shape, a shape that induces mixing in blood flowing past the outlet lumen or in the working fluid,
 wherein the outlet lumen and the inlet lumen are configured such that blood flows between the outlet lumen and the inlet lumen.

2. The catheter system of claim 1, wherein the inlet lumen and the outlet lumen are made of a flexible material.

3. The catheter system of claim 2, wherein the flexible material is a material capable of undergoing inflation.

4. The catheter system of claim 2, wherein the flexible material is rubber.

5. The catheter system of claim 2, wherein the flexible material is capable of undergoing inflation.

6. The catheter system of claim 5, wherein the structure causes the outlet to maintain its approximate uninflated position.

7. The catheter system of claim 1, wherein the working fluid is saline.

8. The catheter system of claim 1, further comprising a working fluid supply including a pump, and wherein the pump circulates the working fluid.

9. The catheter system of claim 1, wherein the structure comprises a wire.

10. The catheter system of claim 1, wherein the outlet lumen is made of a flexible material.

11. A catheter system to rewarm a patient, comprising:
 a working fluid supply configured to circulate a working fluid, wherein the working fluid supply is configured to produce a working fluid at a temperature of greater than about 37° C.;

an inlet lumen to introduce the circulating working fluid; and at least one outlet lumen to extract a circulating working fluid, the outlet lumen having a structure disposed within the outlet lumen to maintain its shape, a shape that induces mixing in blood flowing past the outlet lumen or in the working fluid, wherein the outlet lumen and the inlet lumen are configured such that blood flows between the outlet lumen and the inlet lumen.

12. The catheter system of claim 11, wherein the structure comprises a wire.

13. The catheter system of claim 11, wherein the outlet lumen is made of a flexible material.

14. The catheter system of claim 13, wherein the flexible material is rubber.

15. The catheter system of claim 13, wherein the flexible material is capable of undergoing inflation.

16. The catheter system of claim 15, wherein the structure causes the outlet to maintain its approximate uninflated position.

17. A catheter method of inducing a therapeutic state of hypothermia in a patient comprising:

inserting an inflatable heat transfer element, formed by at least an inlet lumen and a single outlet lumen, into an artery or vein, the outlet lumen having a structure disposed within the outlet lumen to maintain its shape;

inflating the inflatable heat transfer element by delivering a working fluid to the inflatable heat transfer element, the temperature of the working fluid lower than that of the blood; and passing the working fluid through a mixing inducing path formed by the outlet lumen, wherein an open path between the inlet lumen and the outlet lumen allows blood flow therethrough, thereby enhancing heat transfer between the working fluid and the blood, wherein the outlet lumen and the inlet lumen are configured such that blood flows between the outlet lumen and the inlet lumen.

18. A method for warming a body of a patient, comprising:

introducing a catheter having an inflatable heat transfer element, formed by at least an inlet lumen and a single outlet lumen, the outlet lumen having a mixing inducing shape and a structure within the outlet lumen to maintain its shape, into a blood vessel;

circulating a working fluid through the heat transfer element, wherein the working fluid is removed from the heat transfer element by passing through the outlet lumen, the working fluid having a temperature greater than the temperature of the blood vessel; and such that heat is added to the blood to warm the body, wherein the outlet lumen and the inlet lumen are configured such that blood flows between the outlet lumen and the inlet lumen.

* * * * *